US009538905B2

(12) United States Patent
Yamada

(10) Patent No.: US 9,538,905 B2
(45) Date of Patent: Jan. 10, 2017

(54) ADVANCE AND RETREAT ASSIST TOOL FOR ENDOSCOPIC TREATMENT INSTRUMENT

(71) Applicant: OLYMPUS CORPORATION, Tokyo (JP)

(72) Inventor: Tetsuhiro Yamada, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/477,379

(22) Filed: Sep. 4, 2014

(65) Prior Publication Data

US 2015/0045618 A1    Feb. 12, 2015

Related U.S. Application Data

(63) Continuation of application No. PCT/JP2013/083648, filed on Dec. 16, 2013.

(30) Foreign Application Priority Data

Feb. 27, 2013    (JP) ................................ 2013-037222

(51) Int. Cl.
| | |
|---|---|
| *A61B 1/00* | (2006.01) |
| *A61B 1/04* | (2006.01) |
| *A61B 1/018* | (2006.01) |
| *A61B 17/00* | (2006.01) |

(52) U.S. Cl.
CPC ....... *A61B 1/00133* (2013.01); *A61B 1/00128* (2013.01); *A61B 1/018* (2013.01); *A61B 17/00234* (2013.01); *A61B 2017/0034* (2013.01)

(58) Field of Classification Search
USPC ................ 600/102, 104, 106, 107, 114, 115, 121,600/123, 131, 146, 147, 153, 154; 604/528; 606/1, 205
See application file for complete search history.

(56) References Cited

U.S. PATENT DOCUMENTS

| | | | |
|---|---|---|---|
| 2005/0119522 A1 | 6/2005 | Okada | |
| 2005/0119527 A1* | 6/2005 | Banik | ................ A61B 1/00059 600/117 |
| 2014/0171735 A1* | 6/2014 | Galperin | ............ A61B 1/00066 600/106 |

FOREIGN PATENT DOCUMENTS

| | | |
|---|---|---|
| EP | 1905346 A2 | 4/2008 |
| JP | A-09-276211 | 10/1997 |
| JP | A-11-225950 | 8/1999 |
| JP | A-2003-265406 | 9/2003 |
| JP | A-2005-152502 | 6/2005 |
| JP | 2005-218755 A | 8/2005 |
| JP | 2005-230159 A | 9/2005 |
| JP | A-2005-334132 | 12/2005 |

(Continued)

OTHER PUBLICATIONS

International Search Report issued in International Application No. PCT/JP2013/083648 dated Feb. 18, 2014.

(Continued)

*Primary Examiner* — Ryan Henderson
(74) *Attorney, Agent, or Firm* — Oliff PLC

(57) ABSTRACT

An advance and retreat assist tool includes a base unit, an attachment portion which attaches the base unit to a treatment instrument insertion portion so that the base unit is rotatable around a central axis of a treatment instrument insertion hole portion, and a first tubular member. The advance and retreat assist tool further includes a rotary portion and an advance and retreat mechanism.

19 Claims, 19 Drawing Sheets

(56) References Cited

FOREIGN PATENT DOCUMENTS

| | | |
|---|---|---|
| JP | A-2007-159756 | 6/2007 |
| JP | A-2010-057919 | 3/2010 |
| WO | WO 2014/007170 A1 | 1/2014 |

OTHER PUBLICATIONS

Sep. 11, 2015 International Preliminary Report on Patentability issued in International Application No. PCT/JP2013/083648.
Sep. 30, 2016 Search Report issued in European Patent Application No. 13876380.0.

* cited by examiner

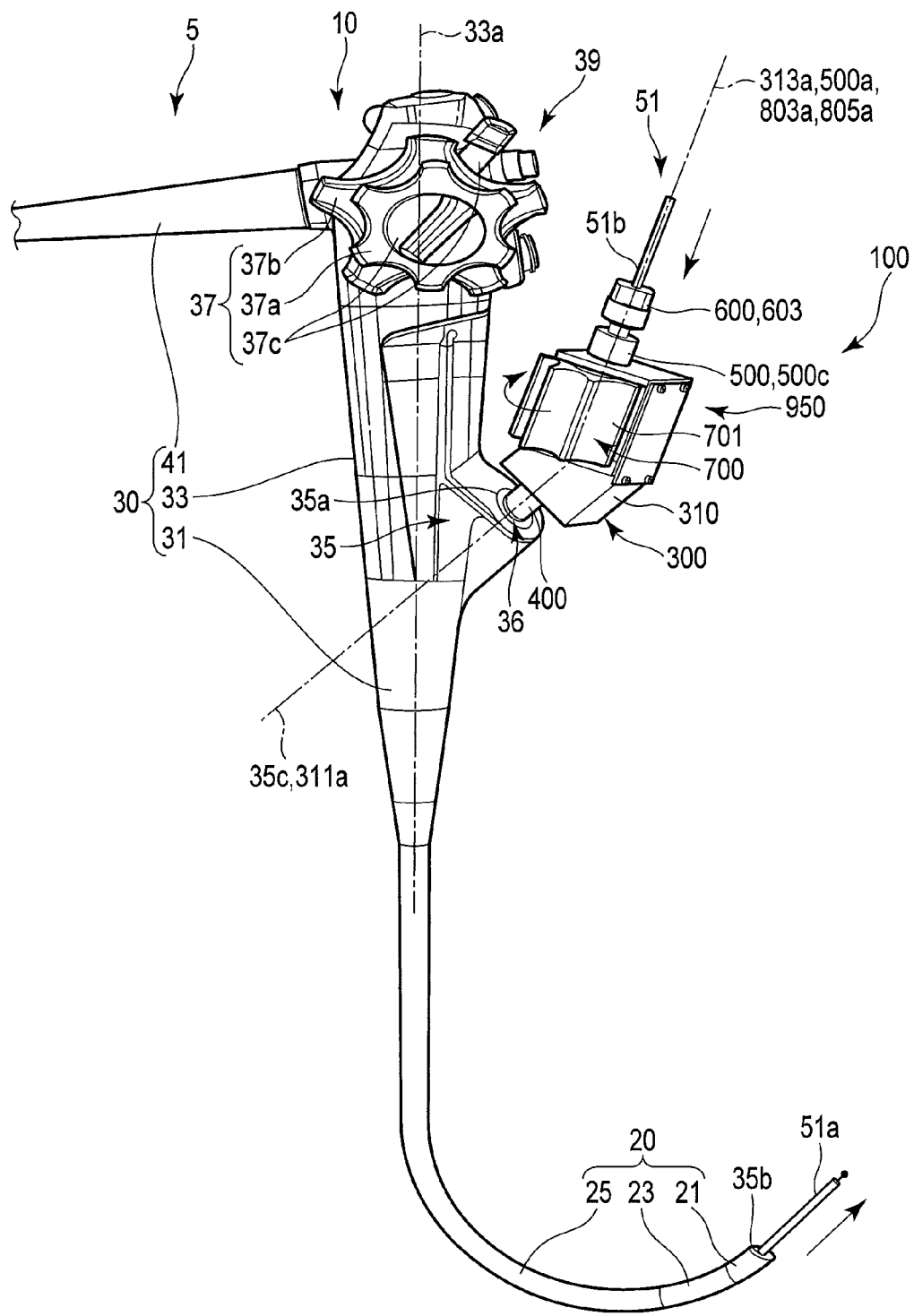
F I G. 1A

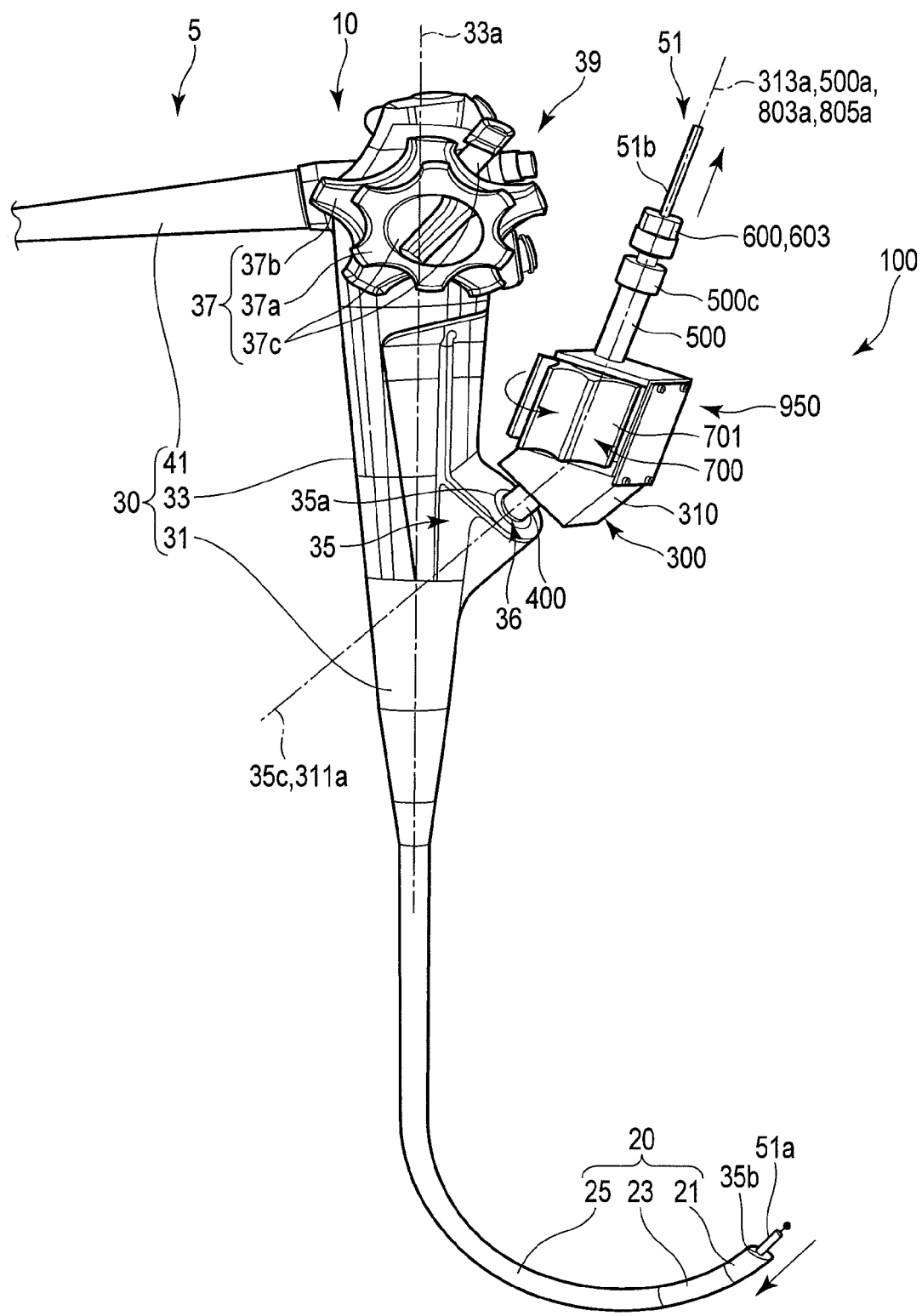
F I G. 1B

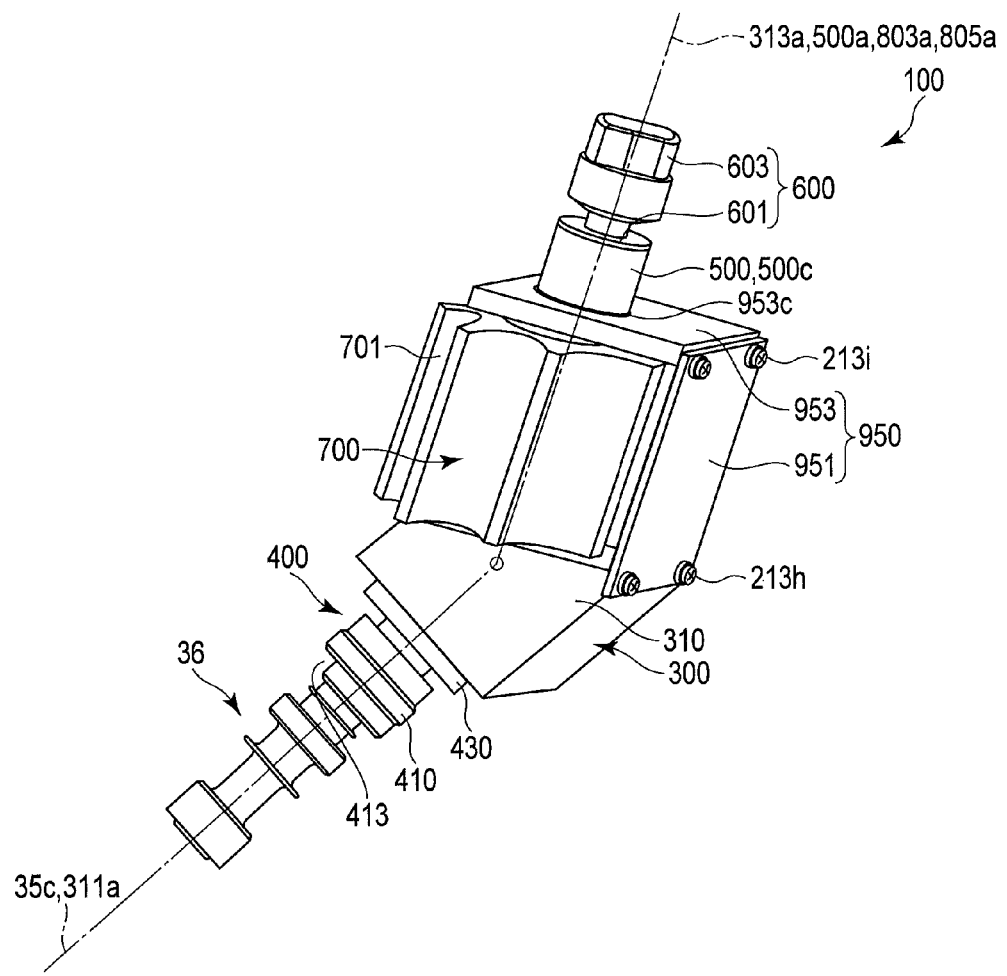
F I G. 2A

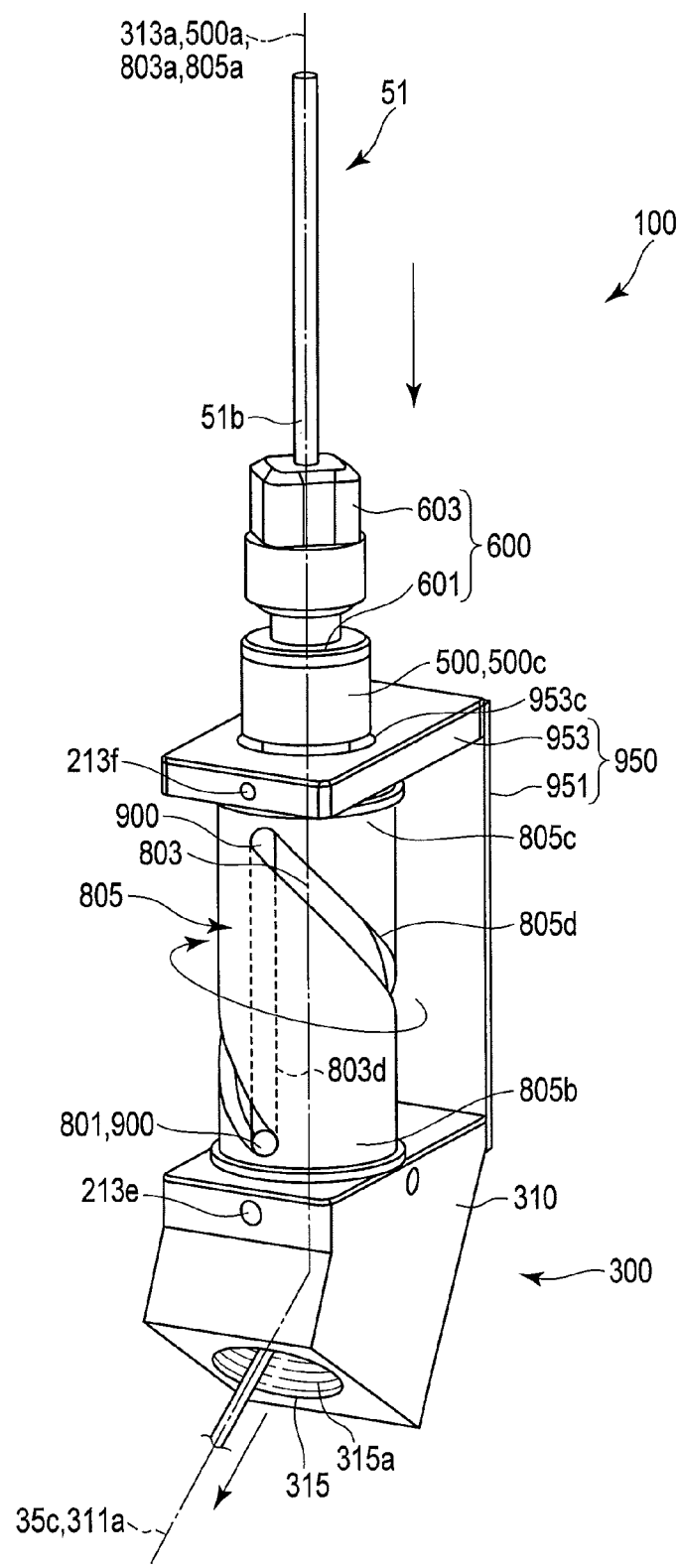
F I G. 3A

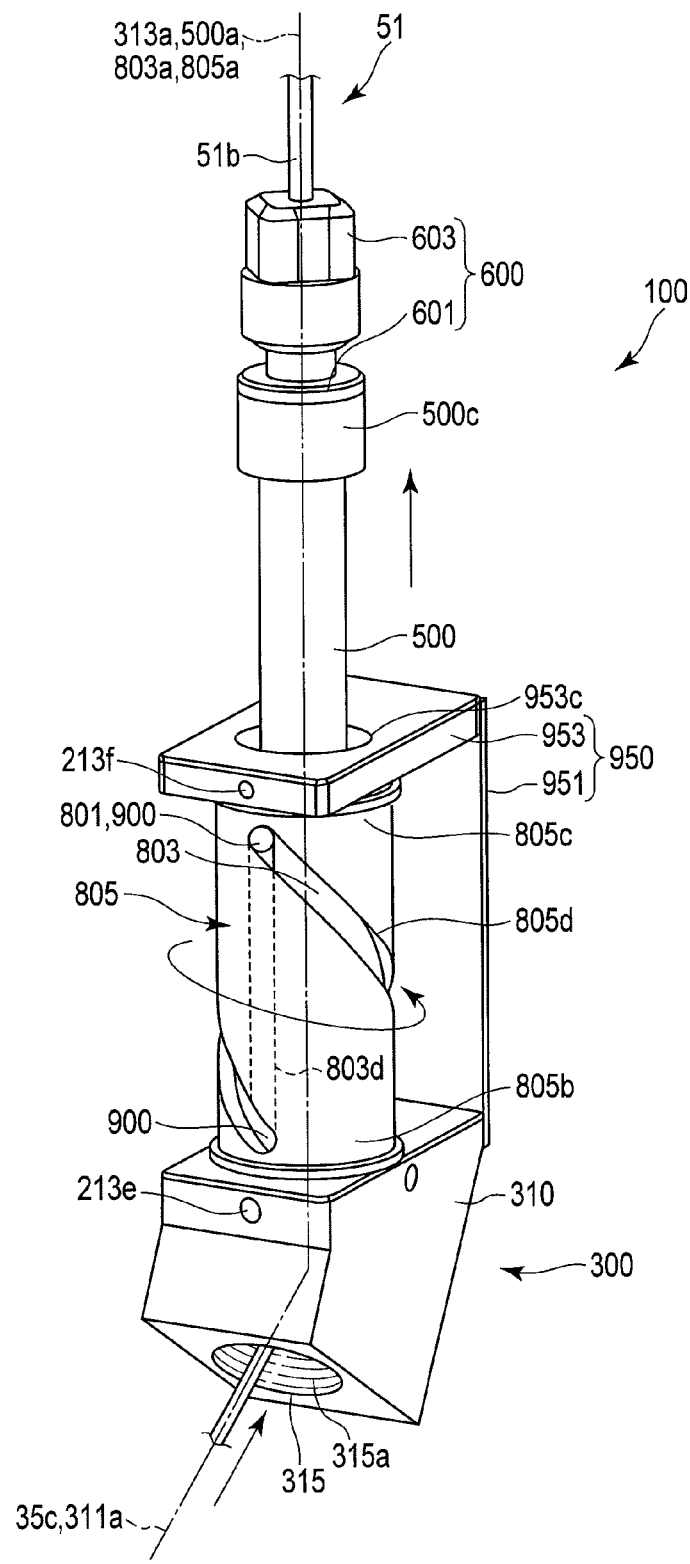
F I G. 3B

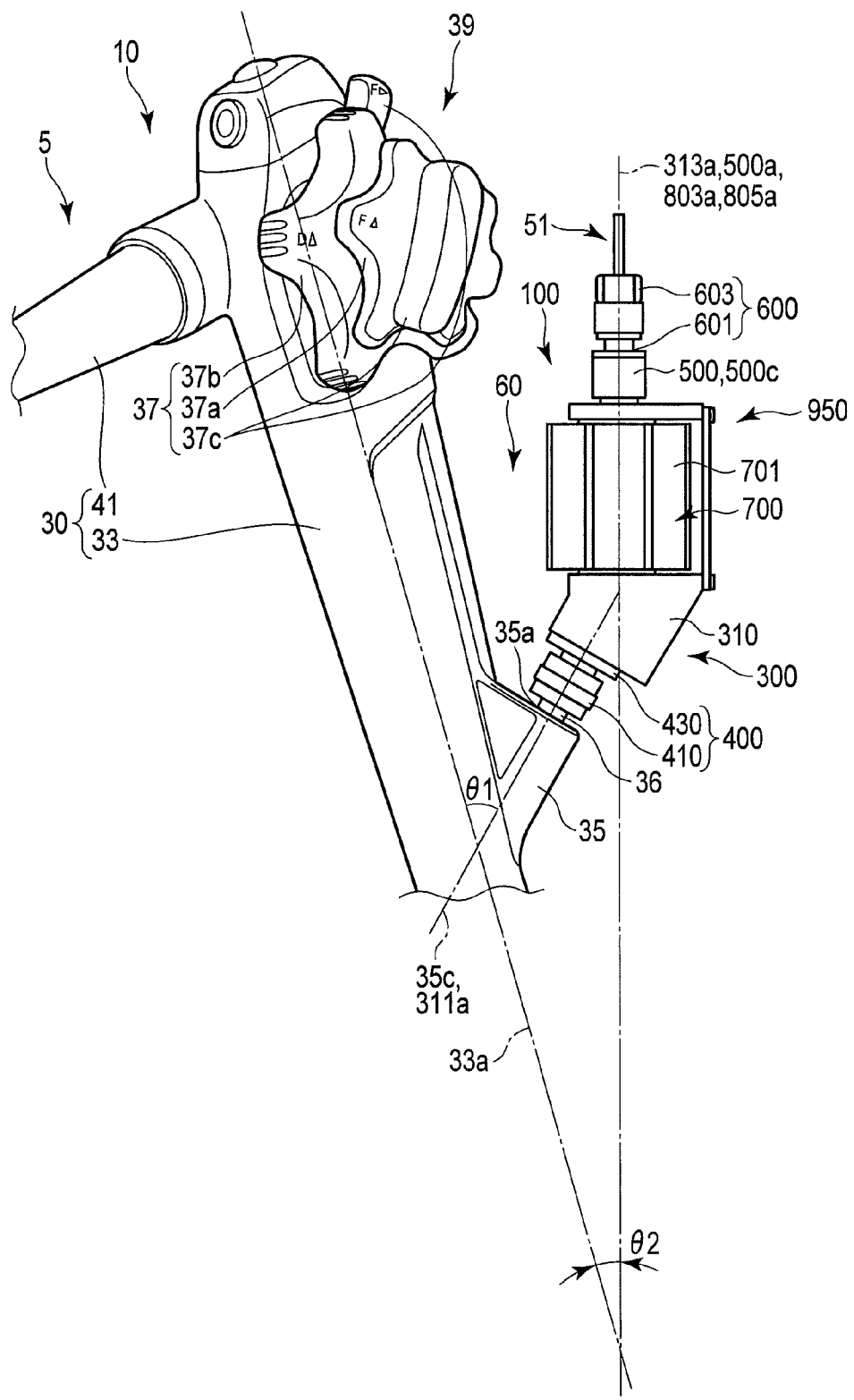
F I G. 5B

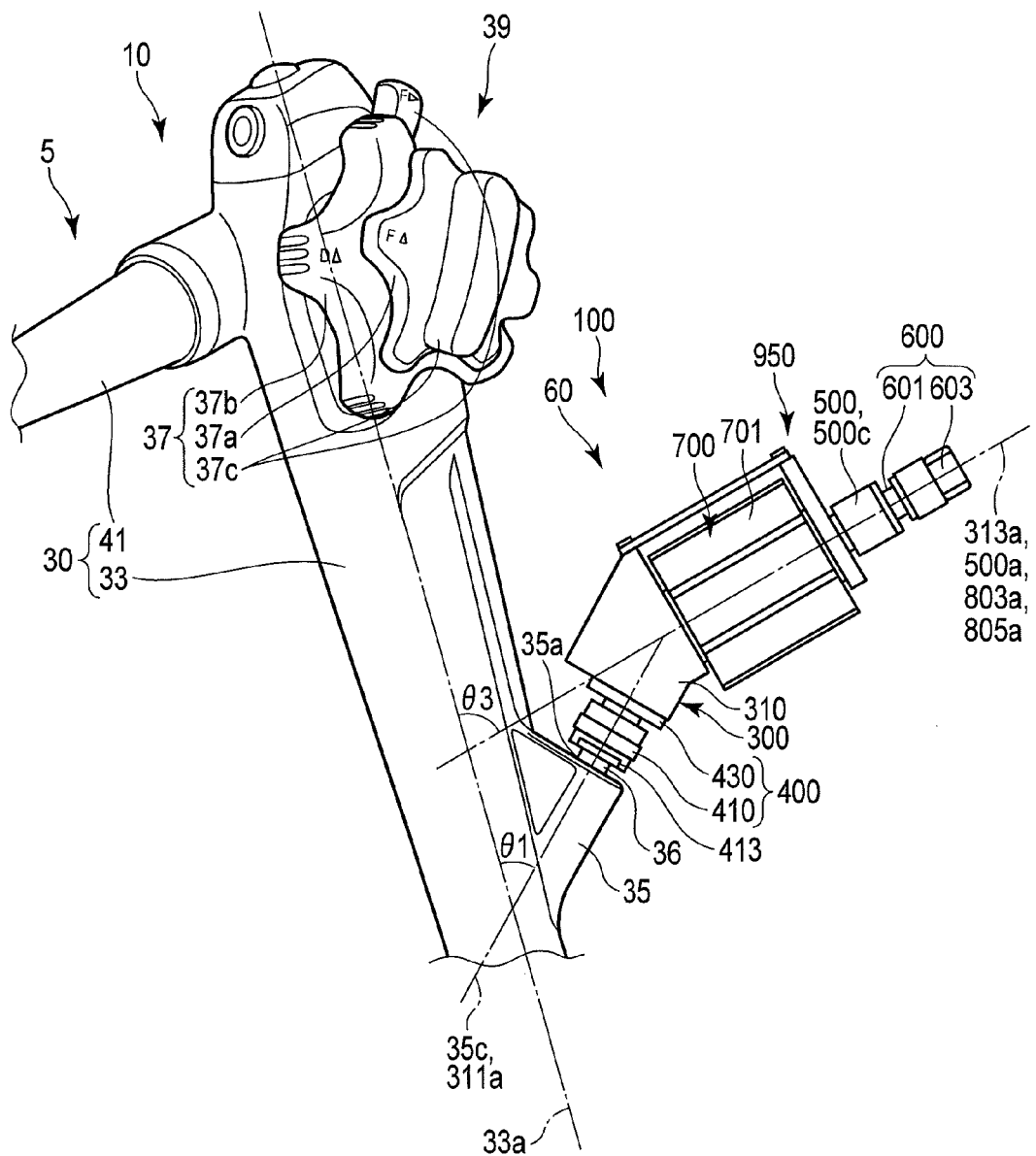
F I G. 5C

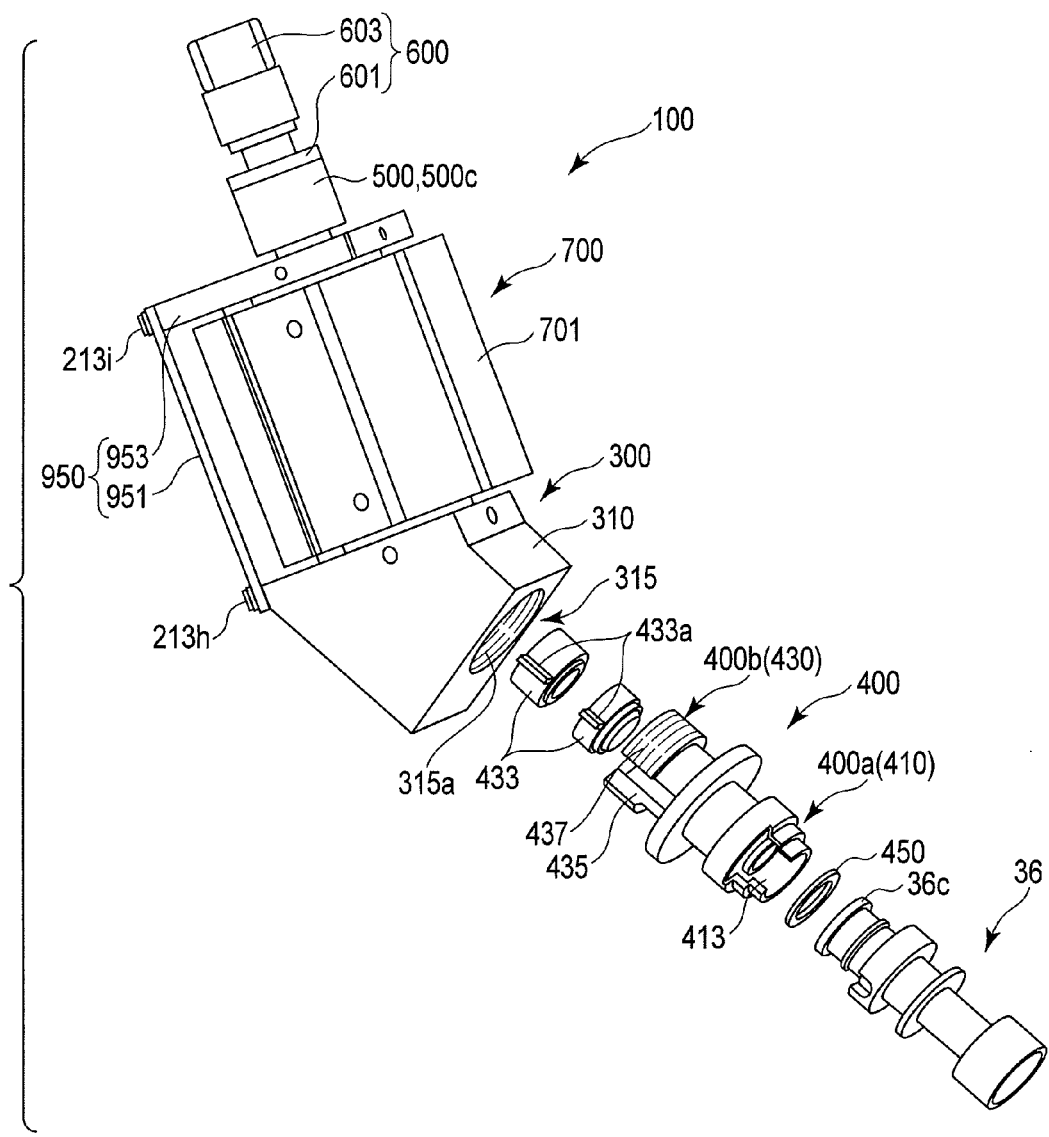
F I G. 6A

ADVANCE AND RETREAT ASSIST TOOL FOR ENDOSCOPIC TREATMENT INSTRUMENT

CROSS-REFERENCE TO RELATED APPLICATIONS

This application is a Continuation Application of PCT Application No. PCT/JP2013/083648, filed Dec. 16, 2013 and based upon and claiming the benefit of priority from prior Japanese Patent Application No. 2013-037222, filed Feb. 27, 2013, the entire contents of all of which are incorporated herein by reference.

BACKGROUND OF THE INVENTION

1. Field of the Invention

The present invention relates to an advance and retreat assist tool for an endoscopic treatment instrument.

2. Description of the Related Art

For example, Jpn. Pat. Appln. KOKAI Publication No. 11-225950, Jpn. Pat. Appln. KOKAI Publication No. 2007-159756, Jpn. Pat. Appln. KOKAI Publication No. 2010-57919, and Jpn. Pat. Appln. KOKAI Publication No. 9-276211 have each disclosed an advance and retreat assist tool for an endoscopic treatment instrument which assists a treatment instrument of an endoscope in advancing and retreating.

For example, in Jpn. Pat. Appln. KOKAI Publication No. 11-225950, Jpn. Pat. Appln. KOKAI Publication No. 2007-159756, Jpn. Pat. Appln. KOKAI Publication No. 2010-57919, and Jpn. Pat. Appln. KOKAI Publication No. 9-276211, the advance and retreat assist tool is attached to a treatment instrument insertion hole portion so that the advance and retreat assist tool is provided straight along the central axis direction of the treatment instrument insertion hole portion provided in a treatment instrument insertion portion. The central axis direction of the treatment instrument insertion hole portion is slanted relative to the central axis direction of a grasping portion. Thus, the advance and retreat assist tool is slanted relative to the central axis direction of the grasping portion.

BRIEF SUMMARY OF THE INVENTION

An aspect of advance and retreat assist tool for an endoscopic treatment instrument of the present is the advance and retreat assist tool includes: base unit comprising a hole portion which has a first central axis and a second central axis slanted relative to the first central axis; an attachment portion which attaches the base unit to a treatment instrument insertion portion provided in a grasping portion of an endoscope so that the side of the hole portion having the first central axis faces a treatment instrument insertion hole portion and so that the base unit is rotatable around the central axis of the treatment instrument insertion hole portion; a first tubular member provided to have an axis along the direction of the second central axis, the endoscopic treatment instrument being inserted into and fixed to the first tubular member; a rotary portion into which the first tubular member is inserted and which rotates around the same axis as the first tubular member; and an advance and retreat mechanism which converts a rotation force during the rotation of the rotary portion to an advance and retreat force along the axial direction of the first tubular member to advance and retreat the first tubular member.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1A is a schematic diagram showing how an advance and retreat assist tool according to a first embodiment of the present invention is attached to an endoscope and how a treatment instrument advances;

FIG. 1B is a schematic diagram showing how the advance and retreat assist tool is attached to the endoscope and how the treatment instrument retreats;

FIG. 2A is a perspective view of the advance and retreat assist tool including a treatment instrument insertion cap;

FIG. 3A is a perspective view of the advance and retreat assist tool during the advance of the treatment instrument;

FIG. 3B is a perspective view of the advance and retreat assist tool during the retreat of the treatment instrument;

FIG. 5B is a schematic diagram in which the angle $\theta 1$>the angle $\theta 2$, the clearance between the grasping portion and the rotation portion is smallest, and the endoscope is grasped and the treatment instrument is advanced and retreated with one hand at the same time;

FIG. 5C is a schematic diagram in which the angle $\theta 3$>the angle $\theta 1$, the clearance between the grasping portion and the rotation portion is widest, and the interruption of the grasping by the advance and retreat assist tool is eliminated;

FIG. 6A is an exploded perspective view of mainly the attachment portion according to a first modification of the first embodiment;

DETAILED DESCRIPTION OF THE INVENTION

Hereinafter, embodiments of the present invention will be described in detail with reference to the drawings.

First Embodiment

Configuration

Figure 1C:
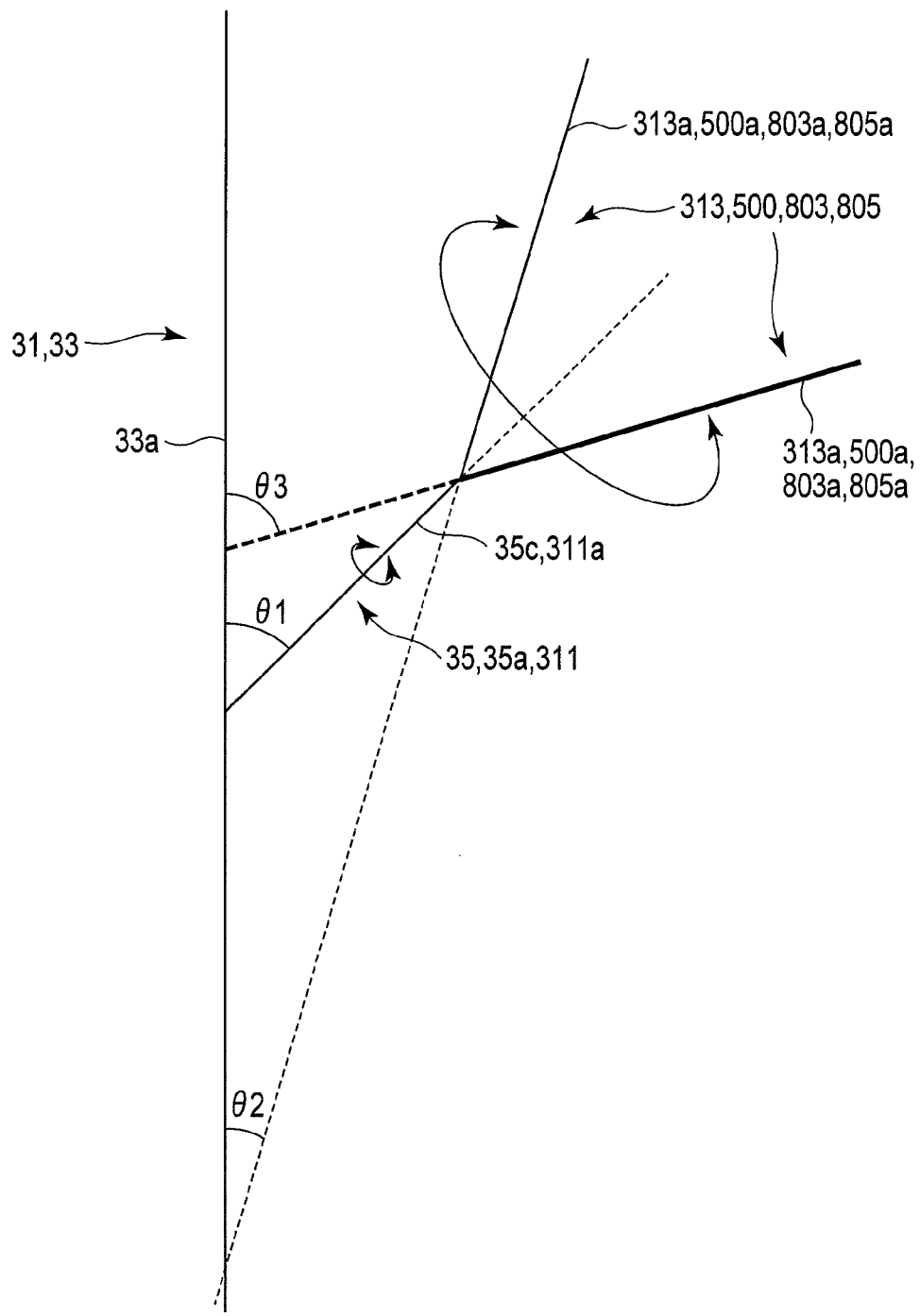
FIG. 1C is a diagram showing the relation between an angle $\theta 1$, an angle $\theta 2$, and an angle $\theta 3$.

The first embodiment is described with reference to FIG. 1A, FIG. 1B, FIG. 1C, FIG. 2A, FIG. 2B, FIG. 2C, FIG. 3A, FIG. 3B, FIG. 3C, FIG. 4A, FIG. 4B, FIG. 5A, FIG. 5B, and FIG. 5C. As an attachment portion 400 and a treatment instrument insertion cap 36 are shown in FIG. 1A in a simplified form, some components are not shown for clarity in some of the drawings.

Figure 3C:
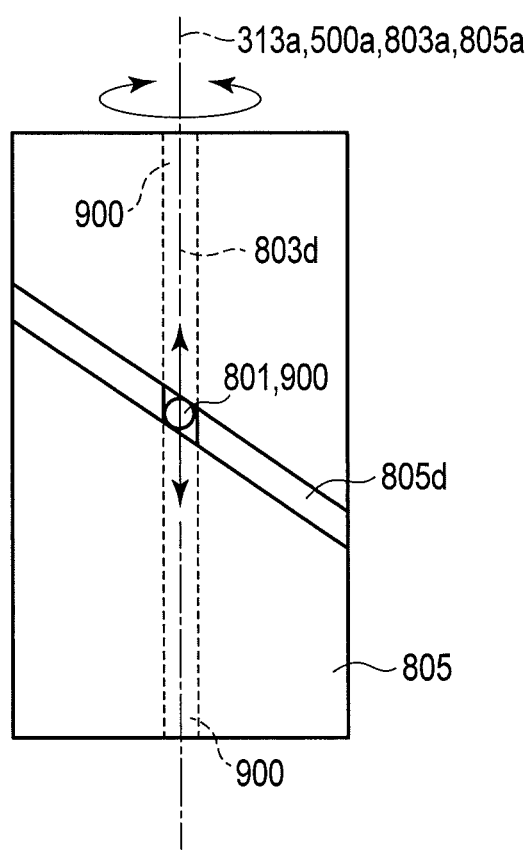
FIG. 3C is a front view showing the relation between a protrusion portion, a long opening portion, and a spiral opening portion during the advance and retreat of the treatment instrument.
Figure 4A:
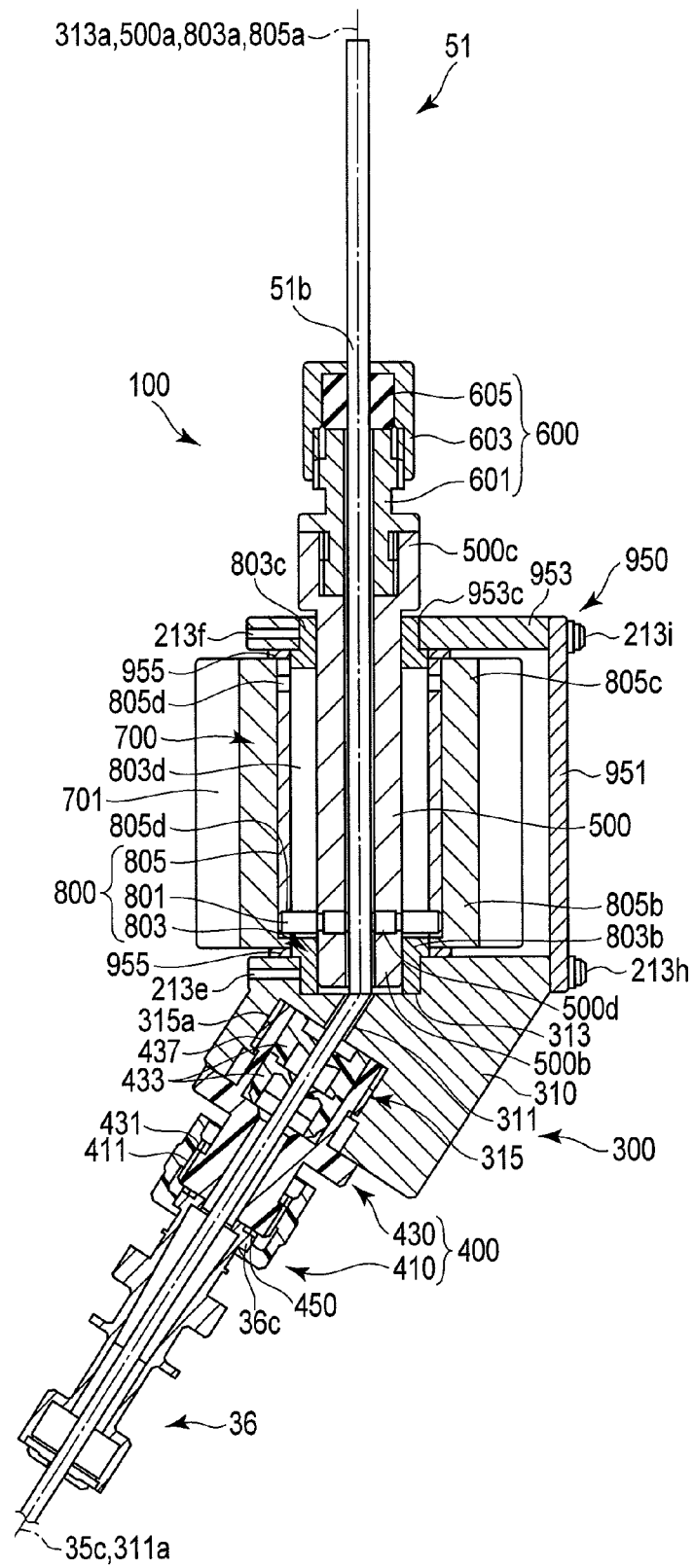
FIG. 4A is a sectional view of the advance and retreat assist tool during the advance of the treatment instrument.

As shown in FIG. 1A, FIG. 3A, and FIG. 4A, the advance of a first tubular member 500 means that the first tubular member 500 moves along the direction of a third central axis 500a so that the first tubular member 500 is inserted into a second tubular member 803.

Figure 4B:
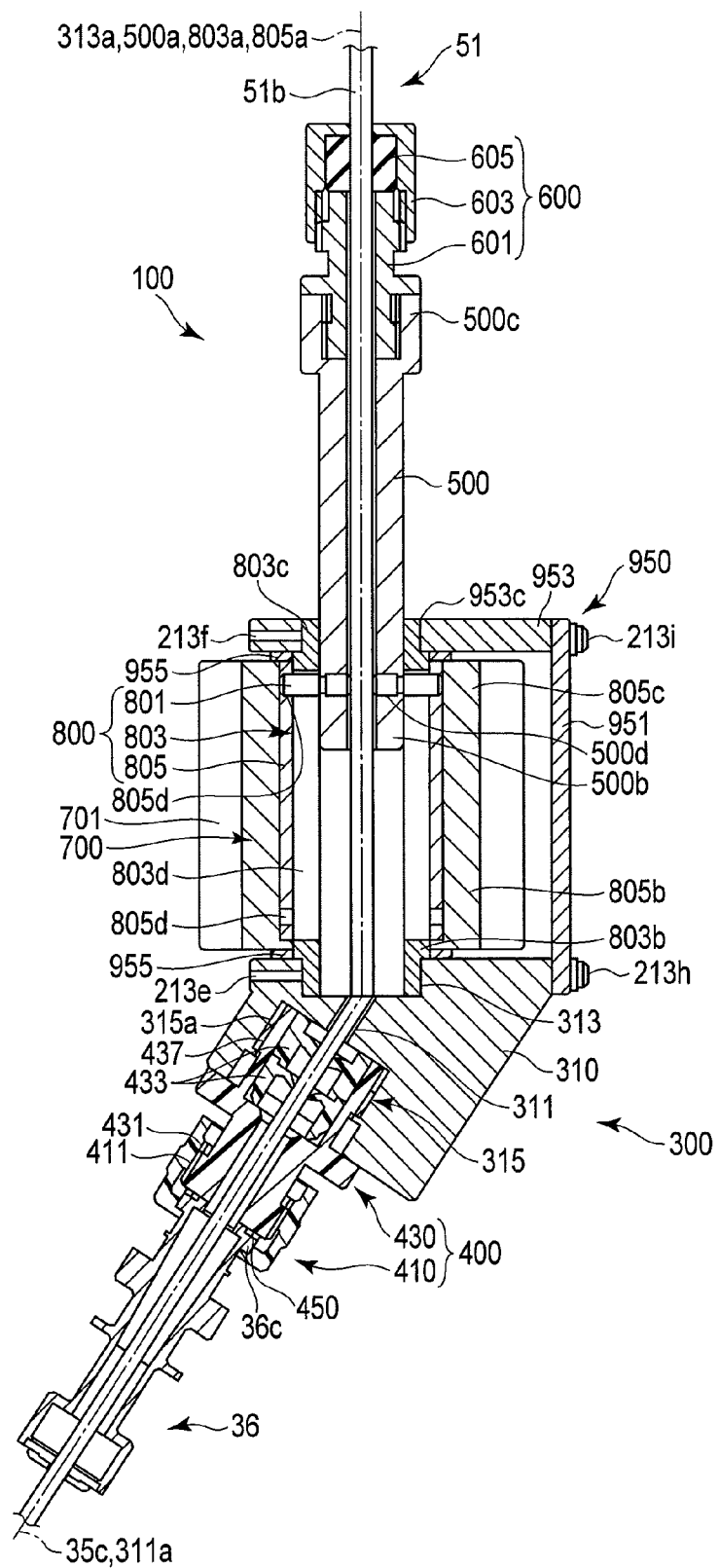
FIG. 4B is a sectional view of the advance and retreat assist tool during the retreat of the treatment instrument.

As shown in FIG. 1B, FIG. 3B, and FIG. 4B, the retreat of the first tubular member 500 means that the first tubular member 500 moves along the direction of the third central axis 500a so that the first tubular member 500 is removed from the second tubular member 803.

As shown in FIG. 1A, FIG. 1B, FIG. 3A, FIG. 3B, FIG. 4A, and FIG. 4B, for example, the advance and retreat of the first tubular member 500 include the advance of the first tubular member 500 and the retreat of the first tubular member 500.

As shown in FIG. 1A, FIG. 3A, and FIG. 4A, for example, the advance of a treatment instrument 51 means that the treatment instrument 51 moves so that the treatment instrument 51 moves to the side of a distal hard portion 21 from the side of an operation portion 30 and a distal end portion 51a of the treatment instrument 51 projects outward from the inside of an insertion portion 20 via a distal opening portion 35b in response to the advance of the first tubular member 500.

As shown in FIG. 1B, FIG. 3B, and FIG. 4B, for example, the retreat of the treatment instrument 51 means that the treatment instrument 51 moves so that the treatment instrument 51 moves to the side of the operation portion 30 from the side of the distal hard portion 21 and the distal end portion 51a of the treatment instrument 51 is housed in the insertion portion 20 from the outside via the distal opening portion 35b in response to the retreat of the first tubular member 500.

As shown in FIG. 1A, FIG. 1B, FIG. 3A, FIG. 3B, FIG. 4A, and FIG. 4B, for example, the advance and retreat of the treatment instrument 51 include the advance of the treatment instrument 51 and the retreat of the treatment instrument 51.

[Endoscopic System 5]

As shown in FIG. 1A and FIG. 1B, an endoscopic system 5 has an endoscope 10, the endoscopic treatment instrument (hereinafter, treatment instrument 51), and an advance and retreat assist tool 100 for the treatment instrument 51.

[Endoscope 10]

The endoscope 10 has a hollow and elongated insertion portion 20 to be inserted into, for example, a body cavity, and the operation portion 30 which is coupled to the proximal end portion of the insertion portion 20 and which operates the endoscope 10.

[Insertion Portion 20]

The insertion portion 20 has the distal hard portion 21, a bending portion 23, and a flexible tubular portion 25 from the distal end portion side of the insertion portion 20 to the proximal end portion side portion of the insertion portion 20. The proximal end portion of the distal hard portion 21 is coupled to the distal end portion of the bending portion 23, and the proximal end portion of the bending portion 23 is coupled to the distal end portion of the flexible tubular portion 25.

The distal hard portion 21 is the distal end portion of the insertion portion 20, and is hard and unbendable. The distal hard portion 21 has the distal opening portion 35b, and an unshown observation window included in an unshown observation optical system. The distal hard portion 21 also has an unshown pair of illumination windows which are provided across the observation window and which are included in an unshown illumination optical system, and a nozzle which supplies air and water to the observation window. The distal opening portion 35b, the observation window, the illumination windows, and the nozzle are provided in a distal end face of the distal hard portion 21.

The bending portion 23 is bent in a desired direction, for example, in an upward, downward, leftward, or rightward direction by the operation of a later-described bending operation portion 37. When the bending portion 23 is bent, the position and direction of the distal hard portion 21 are changed. An observation target is illuminated by unshown illumination light, and the observation target enters into an observation field. This observation target is, for example, an affected part or a lesion in a subject (e.g., body cavity).

The flexible tubular portion 25 has desired flexibility. Therefore, the flexible tubular portion 25 is bent by an external force. The flexible tubular portion 25 is a tubular member extending from a later-described body portion 31 in the operation portion 30.

[Operation Portion 30]

The operation portion 30 has the body portion 31 from which the flexible tubular portion 25 extends, a grasping portion 33 which is coupled to the proximal end portion of the body portion 31 and which is grasped by a surgeon who operates the endoscope 10, and a universal cord 41 connected to the grasping portion 33.

[Grasping Portion 33]

Figure 5A:
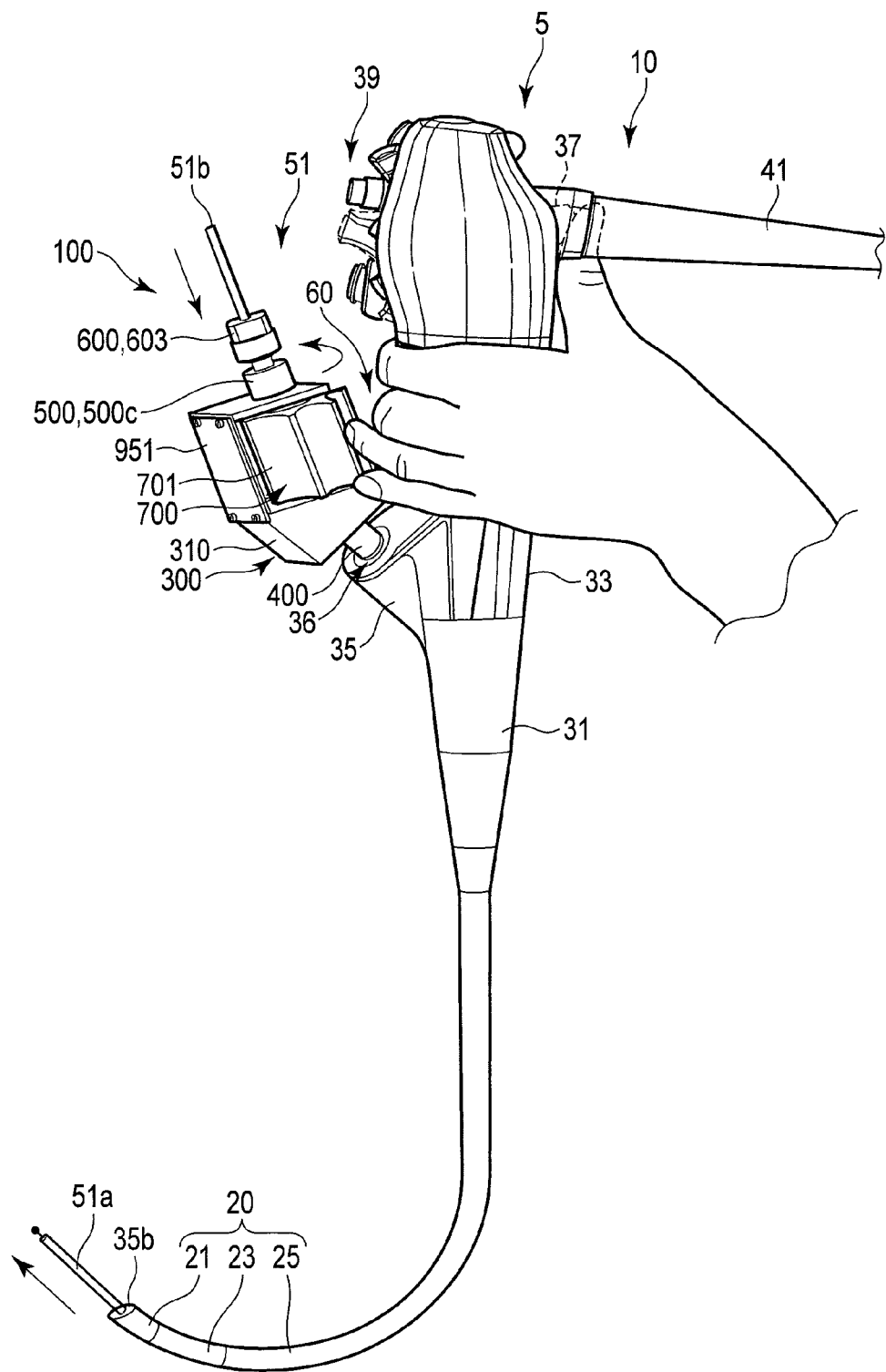
FIG. 5A is a schematic diagram showing how a bending operation portion and a rotation portion are operated by the fingers of the left hand of a surgeon while a grasping portion is being grasped by the left hand in the endoscope to which the advance and retreat assist tool is attached.

The grasping portion 33 has a treatment instrument insertion portion 35, the bending operation portion 37 which is operated to bend the bending portion 23, and a switch portion 39. The treatment instrument insertion portion 35 is provided on the distal end portion side of the grasping portion 33. The bending operation portion 37 and the switch portion 39 are provided on the proximal end portion side of the grasping portion 33. As shown in FIG. 5A, the grasping portion 33 is grasped by the left hand of the surgeon, and the bending operation portion 37 and the switch portion 39 are operated by the fingers of the left hand.

[Treatment Instrument Insertion Portion 35]

The treatment instrument insertion portion 35 branches off from the grasping portion 33. Thus, as shown in FIG. 1A and FIG. 1B, the central axis direction of the treatment instrument insertion portion 35 is slanted relative to the direction of a central axis 33a of the grasping portion 33.

As shown in FIG. 1A and FIG. 1B, the treatment instrument insertion portion 35 has a treatment instrument insertion hole portion 35a which is provided at the end portion of the treatment instrument insertion portion 35 and which is used to insert the treatment instrument 51 into the endoscope 10.

The treatment instrument insertion hole portion 35a is coupled to the proximal end portion of an unshown treatment instrument insertion channel. The treatment instrument insertion channel is provided inside the insertion portion 20, and provided from the flexible tubular portion 25 to the distal hard portion 21 via the bending portion 23. The distal end portion of the treatment instrument insertion channel is in communication with the distal opening portion 35b provided in the distal hard portion 21. The treatment instrument insertion hole portion 35a is an insertion hole portion used to insert the treatment instrument 51 into the treatment instrument insertion channel.

As shown in FIG. 1A and FIG. 1B, a central axis 35c of the treatment instrument insertion hole portion 35a is provided coaxially with the central axis of the treatment instrument insertion portion 35, and is thus slanted relative to the central axis 33a of the grasping portion 33. The direction of the central axis 35c is slanted relative to the direction of the central axis 33a of the grasping portion 33.

As shown in FIG. 1A, FIG. 1B, FIG. 2A, FIG. 2B, FIG. 2C, FIG. 4A, FIG. 4B, FIG. 5A, FIG. 5B, and FIG. 5C, the treatment instrument insertion portion 35 further has a cylindrical treatment instrument insertion cap 36 to be inserted into the treatment instrument insertion hole portion 35a. The treatment instrument insertion cap 36 is made of, for example, a metal. The central axis of the treatment instrument insertion cap 36 is provided coaxially with the central axis 35c of the treatment instrument insertion hole portion 35a. Thus, the treatment instrument insertion cap 36 is slanted relative to the grasping portion 33. When the cylindrical treatment instrument insertion cap 36 is inserted in the treatment instrument insertion hole portion 35a, the treatment instrument insertion cap 36 is in communication with the treatment instrument insertion channel.

The treatment instrument 51 is inserted into the treatment instrument insertion channel from the treatment instrument insertion hole portion 35a via the treatment instrument insertion cap 36, and pressed to the side of the distal hard portion 21. As shown in FIG. 1A and FIG. 1B, the treatment instrument 51 is then projected from the distal opening portion 35b.

As shown in FIG. 1A, FIG. 1B, FIG. 2A, FIG. 2B, FIG. 2C, FIG. 4A, FIG. 4B, FIG. 5A, FIG. 5B, and FIG. 5C, the advance and retreat assist tool 100 is attached to the treatment instrument insertion cap 36. In this case, the treatment instrument insertion cap 36 is brought into communication with a first hole portion 311 of a later-described base member 310.

As shown in FIG. 2B, FIG. 2C, FIG. 4A, and FIG. 4B, the treatment instrument insertion cap 36 has a distal end portion to be inserted into the treatment instrument insertion hole portion 35a, and a proximal end portion which projects outward from the treatment instrument insertion hole portion 35a and which is exposed to the outside. The proximal end portion has an edge portion 36c. The edge portion 36c is formed as an outer flange, and is folded outward in the diametrical direction of the treatment instrument insertion cap 36.

[Bending Operation Portion 37]

The bending operation portion 37 has a horizontal bending operation knob 37a which is operated to horizontally bend the bending portion 23, a vertical bending operation knob 37b which is operated to vertically bend the bending portion 23, and a fixing knob 37c which fixes the position of the bent bending portion 23.

[Switch Portion 39]

The switch portion 39 is operated by the hand of the surgeon when the grasping portion 33 is grasped by the surgeon. The switch portion 39 is operated during the operation of various functions of the endoscope such as air supply, water supply, suction, and photography.

[Universal Cord 41]

The universal cord 41 has an unshown connector which can be attached to and removed from an unshown control apparatus.

[Treatment Instrument 51]

The treatment instrument 51 is formed by, for example, an elongated linear member.

[Advance and Retreat Assist Tool 100]

As shown in FIG. 1A and FIG. 1B, the advance and retreat assist tool 100 is removably attached to the endoscope 10, in particular, the treatment instrument insertion portion 35. More specifically, as shown in FIG. 1C, FIG. 5B and FIG. 5C, the advance and retreat assist tool 100 is removably attached to the treatment instrument insertion cap 36 which is inserted into the treatment instrument insertion hole portion 35a of the treatment instrument insertion portion 35 so that the advance and retreat assist tool 100 is rotatable around the central axis of the treatment instrument insertion cap 36 (the central axis 35c of the treatment instrument insertion hole portion 35a). The advance and retreat assist tool 100 assists the treatment instrument 51 in advancing and retreating along the longitudinal axis direction of the treatment instrument 51. The treatment instrument 51 is inserted in the endoscope 10 from the treatment instrument insertion hole portion 35a via the treatment instrument insertion cap 36. The distal end portion 51a of the treatment instrument 51 can project from the distal opening portion 35b.

As shown in FIG. 1A FIG. 1B, FIG. 1C, FIG. 5A, FIG. 5B, and FIG. 5C, the advance and retreat assist tool 100 has a base unit 300, and the attachment portion 400 which removably attaches the base unit 300 to the treatment instrument insertion portion 35 (the treatment instrument insertion cap 36) so that the base unit 300 is rotatable around the central axis 35c of the treatment instrument insertion hole portion 35a (the treatment instrument insertion cap 36). As shown in FIG. 1A FIG. 1B, FIG. 5A, FIG. 5B, and FIG. 5C, the advance and retreat assist tool 100 further has the first tubular member 500 through which the treatment instrument 51 is inserted and which guides the treatment instrument 51 to the endoscope 10 via the base unit 300, and a fixing portion 600 which fixes the treatment instrument 51 to the first tubular member 500. As shown in FIG. 1A, FIG. 1B, FIG. 2A, FIG. 2B, FIG. 3A, FIG. 3B, FIG. 3C, FIG. 4A, FIG. 4B, FIG. 5A, FIG. 5B, and FIG. 5C, the advance and retreat assist tool 100 further has a rotary portion 700 provided in the first tubular member 500, and an advance and retreat mechanism 800 which advances and retreats the first tubular member 500 by a rotation force of the rotary portion 700. The advance and retreat assist tool 100 further has a regulating mechanism 900 which regulates the advance and retreat of the first tubular member 500, and a support unit 950 which supports the first tubular member 500 so that the first tubular member 500 advances and retreats.

[Base Unit 300]

Figure 2B:
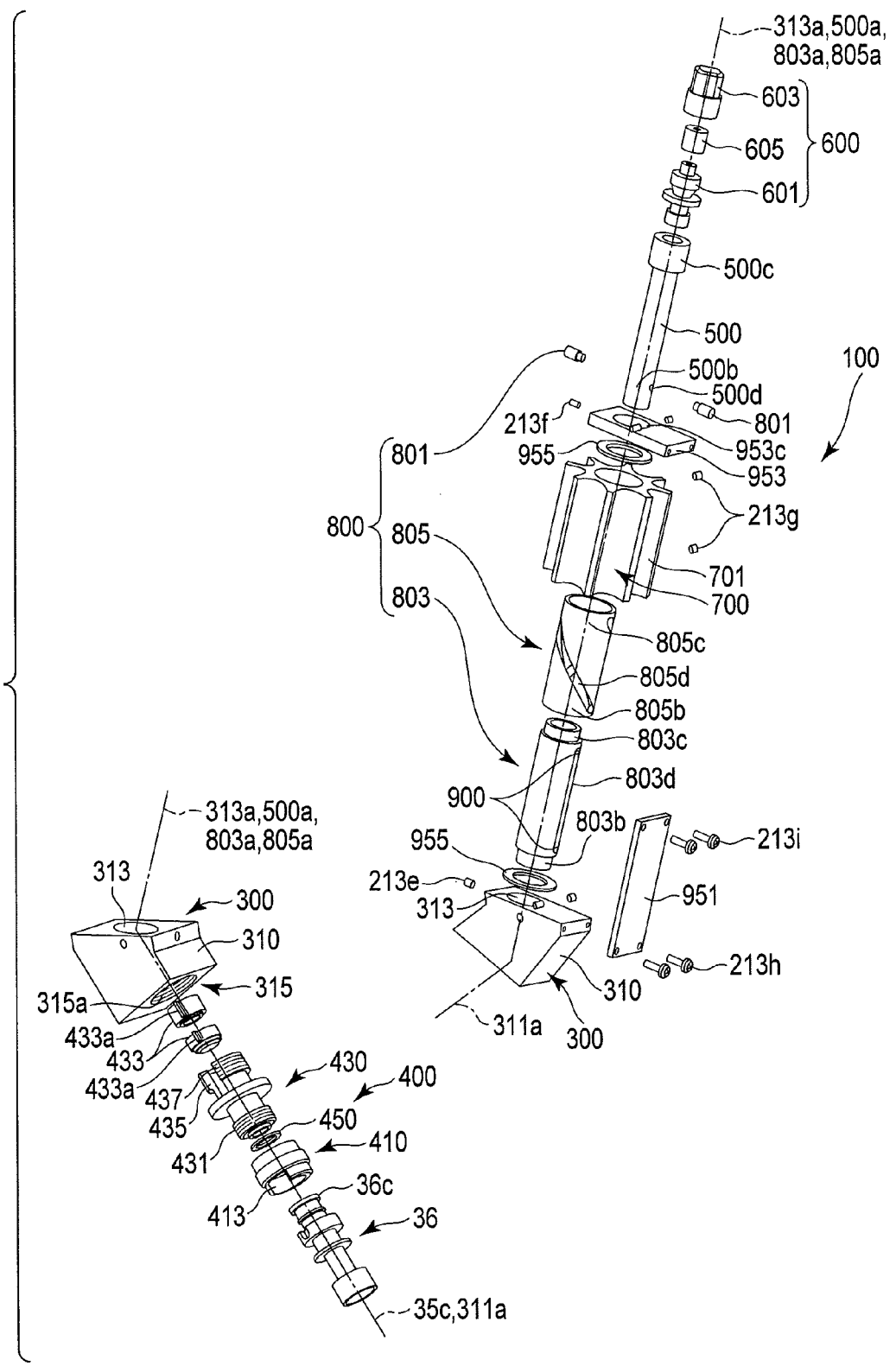
FIG. 2B is an exploded perspective view of the advance and retreat assist tool seen from the side of a cutout portion in an attachment portion.

As shown in FIG. 1A, FIG. 1B, FIG. 2A, FIG. 2B, FIG. 2C, FIG. 3A, FIG. 3B, FIG. 4A, FIG. 4B, FIG. 5A, FIG. 5B, and FIG. 5C, the base unit 300 is removably attached to the treatment instrument insertion cap 36 by the attachment portion 400. The base unit 300 is also attached to the treatment instrument insertion cap 36 by the attachment portion 400 rotatably relative to the treatment instrument insertion cap 36 around the central axis of the treatment instrument insertion cap 36. As shown in FIG. 2A and FIG. 2B, the base unit 300 has the base member 310.

As shown in FIG. 1A and FIG. 1B, the base member 310 is provided to face the treatment instrument insertion hole portion 35a in the direction of the central axis 35c of the treatment instrument insertion hole portion 35a when the advance and retreat assist tool 100 is attached to the endoscope 10.

[Base Member 310]

As shown in FIG. 4A and FIG. 4B, the base member 310 has the first hole portion 311 which has a first central axis 311a, and a second hole portion 313 which has a second central axis 313a slanted relative to the first central axis 311a and which is in communication with the first hole portion 311.

The first hole portion 311 faces the inside of the treatment instrument insertion cap 36 and the treatment instrument insertion channel when the advance and retreat assist tool 100 is attached to the endoscope 10. At the same time, as shown in FIG. 1A, FIG. 1B, and FIG. 1C, the first central axis 311a of the first hole portion 311 is provided coaxially with the central axis 35c of the treatment instrument insertion hole portion 35a, and is slanted relative to the central axis 33a of the grasping portion 33. As shown in FIG. 1C, the second central axis 313a of the second hole portion 313 is slanted relative to the central axis 35c of the treatment instrument insertion hole portion 35a.

The first hole portion 311 is in communication with the outside in one end face of the base member 310, and the second hole portion 313 is in communication with the outside in the other end face of the base member 310. The first hole portion 311 is depressed in one end face of the base member 310. The second hole portion 313 is depressed in the other end face of the base member 310.

As shown in FIG. 4A and FIG. 4B, the first hole portion 311 and the second hole portion 313 function as guide hole portions which guide, to the treatment instrument insertion hole portion 35a via the attachment portion 400 and the treatment instrument insertion cap 36, the treatment instrument 51 which is inserted through the first tubular member 500. The first hole portion 311 has substantially the same diameter as that of the treatment instrument 51. The second hole portion 313 also functions as an insertion hole portion into which the first tubular member 500 is inserted. The second hole portion 313 is larger than the first hole portion 311.

As shown in FIG. 2B, FIG. 2C, FIG. 4A, and FIG. 4B, the base member 310 further has a third hole portion 315 which is in communication with the first hole portion 311 and which is larger than the first hole portion 311. The central axis of the third hole portion 315 is provided coaxially with the first central axis 311a of the first hole portion 311. The third hole portion 315 is in communication with the outside in one end face of the base member 310, and is depressed in one end face of the base member 310. The third hole portion 315 is provided outside the first hole portion 311, in particular, provided on the side of the treatment instrument insertion cap 36. Thus, one end portion of the first hole portion 311 is in communication with the second hole portion 313, and the other end portion of the first hole portion 311 is in communication with the third hole portion 315. A support portion 430 of the attachment portion 400 is screwed into the third hole portion 315.

[Attachment Portion 400]

As shown in FIG. 1A, FIG. 1B, FIG. 1C, FIG. 4A, FIG. 4B, FIG. 5A, FIG. 5B, and FIG. 5C, the attachment portion 400 removably attaches the base unit 300 to the treatment instrument insertion portion 35 (the treatment instrument insertion cap 36) so that the first central axis 311a is provided coaxially with the central axis 35c of the treatment instrument insertion hole portion 35a, so that the first hole portion 311 faces the treatment instrument insertion hole portion 35a, and so that the base member 310 of the base unit 300 is rotatable around the central axis 35c of the treatment instrument insertion hole portion 35a (the central axis of the treatment instrument insertion cap 36).

As shown in FIG. 2A, FIG. 2B, FIG. 2C, FIG. 4A, FIG. 4B, FIG. 5B, and FIG. 5C, the attachment portion 400 has a cylindrical body portion 410 which is removably attached to the treatment instrument insertion cap 36 so that the body portion 410 is rotatable around the central axis 35c of the treatment instrument insertion hole portion 35a, and the cylindrical support portion 430 which is removably attached to the body portion 410 and which supports the base member 310. The body portion 410 is independent of the support portion 430. The body portion 410 and the support portion 430 are comprised of an elastic material such as a resin or rubber.

[Attachment of Body Portion 410 and Support Portion 430]

As shown in FIG. 4A and FIG. 4B, the body portion 410 has a body thread groove portion 411 formed in the inner circumferential surface of the body portion 410. The body thread groove portion 411 is provided at the proximal end portion of the body portion 410.

As shown in FIG. 2B, FIG. 2C, FIG. 4A, and FIG. 4B, the support portion 430 has a distal end support thread groove portion 431 which is formed in the outer circumferential surface of the support portion 430 and which meshes with the body thread groove portion 411. The distal end support thread groove portion 431 is provided at the distal end portion of the support portion 430.

Figure 2C:
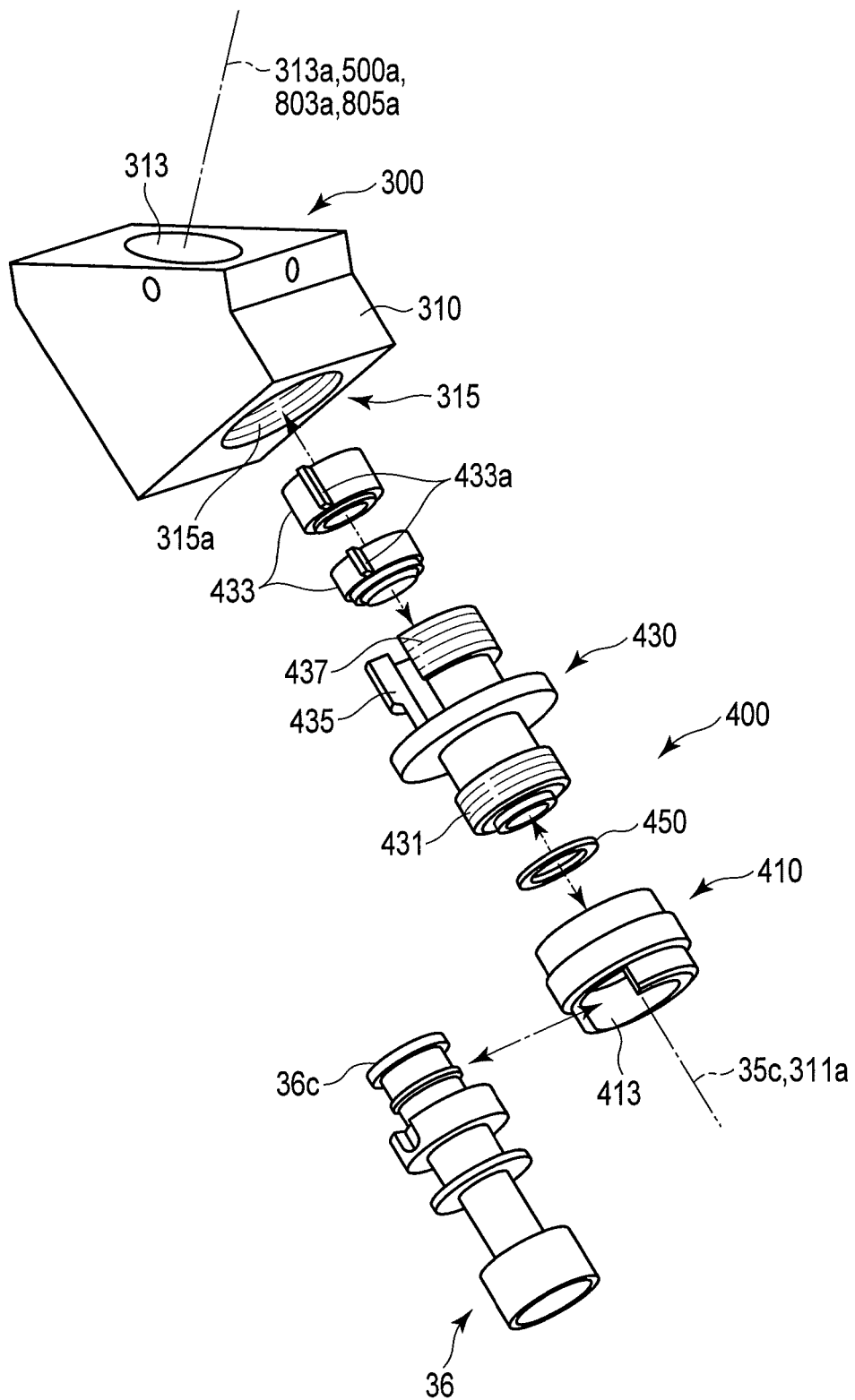
FIG. 2C is a diagram illustrating the attachment of a body portion and a support portion, the attachment of the body portion to the treatment instrument insertion cap, and the attachment of the support portion to the base member.

The support portion 430 is attached to the body portion 410 when the support portion 430 is screwed into the body portion 410 in the central axis direction of the attachment portion 400 as shown in FIG. 2C so that the body thread groove portion 411 and the distal end support thread groove portion 431 mesh with each other while the body portion 410 is attached to the treatment instrument insertion cap 36. Thus, the body portion 410 and the support portion 430 fasten to each other. At the same time, the body portion 410 and the support portion 430 communicate with the treatment instrument insertion cap 36.

As shown in FIG. 4A, and FIG. 4B, when the support portion 430 is attached to the body portion 410, the edge portion 36c of the treatment instrument insertion cap 36 which is formed as the outer flange is provided between the support portion 430 and a distal end portion of the body portion 410 formed as an inner flange in the direction of the central axis 35c of the treatment instrument insertion hole portion 35a. The support portion 430 is attached to the body portion 410 so that the support portion 430 presses the edge portion 36c into the distal end portion of the body portion 410. Thus, the attachment portion 400 is fixed to the treatment instrument insertion cap 36.

As shown in FIG. 2B, FIG. 2C, FIG. 4A, and FIG. 4B, the advance and retreat assist tool 100 further has an interference prevention member 450 which intervenes between the support portion 430 and the edge portion 36c of the treatment instrument insertion cap 36 in the direction of the central axis 35c of the treatment instrument insertion hole portion 35a and which prevents interference between the support portion 430 and the edge portion 36c. The interference prevention member 450 is made of, for example, PTFE. The interference prevention member 450 is in close contact with the support portion 430 and the edge portion 36c of the treatment instrument insertion cap 36.

[Body Portion 410]

As shown in FIG. 2A, FIG. 2B, and FIG. 2C, the body portion 410 has a cutout portion 413 which is formed by the depression of a part of the edge portion of the body portion 410 in the central axis direction of the body portion 410. The cutout portion 413 is provided at the distal end portion of the body portion 410. The cutout portion 413 is not provided flush with the body thread groove portion 411, and is provided closer to the side of the treatment instrument insertion hole portion 35a than the body thread groove portion 411. The cutout portion 413 is not formed over the entire circumference of the body portion 410 in the circumferential direction of the body portion 410, but is formed in a size smaller than, for example, a semicircle. This cutout portion 413 is in communication with the inside of body portion 410 in the diametrical direction of the body portion 410.

As described above, the distal end portion of the body portion 410 is folded inward as the inner flange.

[Attachment of Body Portion 410 to Treatment Instrument Insertion Cap 36]

The body portion 410 is not attached to the treatment instrument insertion cap 36 by being fitted into the proximal end portion of the treatment instrument insertion cap 36 in the axial direction of the treatment instrument insertion cap 36. As shown in FIG. 2C, the cutout portion 413 functions as a head, and the body portion 410 is pressed into the proximal end portion of the treatment instrument insertion cap 36 from the cutout portion 413 in the diametrical direction of the body portion 410. That is, the body portion 410 is pressed into the proximal end portion of the treatment instrument insertion cap 36 from the side surface of the treatment instrument insertion portion 35 via the cutout portion 413 in the diametrical direction of the body portion 410, and is thereby fitted into the proximal end portion of the treatment instrument insertion cap 36, and attached to the proximal end portion of the treatment instrument insertion cap 36. In other words, the proximal end portion of the treatment instrument insertion cap 36 is fitted into the body portion 410 in the diametrical direction of the body portion 410 via the cutout portion 413. Thus, the body portion 410 is attached to the proximal end portion of the treatment instrument insertion cap 36, and the proximal end portion of the treatment instrument insertion cap 36 is provided inside the body portion 410. In this instance, as shown in FIG. 4A, and FIG. 4B, the distal end portion of the body portion 410 formed as the inner flange is caught on the edge portion 36c of the treatment instrument insertion cap 36 formed as the outer flange. In this state, as shown in FIG. 5B, and FIG. 5C, the body portion 410 is rotatable relative to the treatment instrument insertion cap 36 around the central axis 35c of the treatment instrument insertion hole portion 35a.

When the body portion 410 is detached from the treatment instrument insertion cap 36, the body portion 410 is pulled relative to the proximal end portion of the treatment instrument insertion cap 36 in the diametrical direction of the body portion 410 via the cutout portion 413 and then detached from the proximal end portion of the treatment instrument insertion cap 36, in reverse order from the above.

[Support Portion 430]

As shown in FIG. 2B, FIG. 2C, FIG. 4A, and FIG. 4B, in the support portion 430 which supports the base member 310 of the base unit 300, the support portion 430 is attached to the body portion 410 so that the first central axis 311a of the first hole portion 311 is provided coaxially with the central axis 35c of the treatment instrument insertion hole portion 35a and so that the first hole portion 311 faces the treatment instrument insertion hole portion 35a.

As shown in FIG. 2B, FIG. 2C, FIG. 4A, and FIG. 4B, the support portion 430 has a distal end portion which is screwed into the body portion 410, and a proximal end portion which is screwed into the third hole portion 315 and thereby supports the base member 310. The proximal end is screwed into the third hole portion 315 so that the support portion 430 communicates with the first hole portion 311.

As shown in FIG. 2B, FIG. 2C, FIG. 4A, and FIG. 4B, the support portion 430 has a watertight member 433 which is provided inside the proximal end portion of the support portion 430 and which keeps the base member 310 and the support portion 430 watertight. The watertight member 433 has, for example, a ring-shaped packing.

As shown in FIG. 2B and FIG. 2C, the watertight member 433 has a protrusion portion 433a provided in the outer circumferential surface of the watertight member 433. The protrusion portion 433a slides on a slide groove 435 formed in the proximal end portion of the support portion 430 when the watertight member 433 is inserted into and removed from the proximal end portion of the support portion 430. The protrusion portion 433a is grasped when the watertight member 433 is inserted into and removed from the proximal end portion of the support portion 430, and is provided to position the watertight member 433 in the circumferential direction of the support portion 430.

[Attachment of Support Portion 430 to Base Member 310]

As shown in FIG. 2B, FIG. 2C, FIG. 4A, and FIG. 4B, the base member 310 further has a base thread groove portion 315a formed in the inner circumferential surface of the third hole portion 315.

As shown in FIG. 2B, FIG. 2C, FIG. 4A, and FIG. 4B, the support portion 430 further has a proximal support thread groove portion 437 which is formed in the outer circumferential surface of the support portion 430 and which meshes with the base thread groove portion 315a. The proximal support thread groove portion 437 is provided at the proximal end portion of the support portion 430.

The support portion 430 is screwed into the third hole portion 315 in the central axis direction of the attachment portion 400 as shown in FIG. 2C, FIG. 4A, and FIG. 4B so that the base thread groove portion 315a and the proximal support thread groove portion 437 mesh with each other, and the support portion 430 is thereby attached to the base member 310. Thus, the base member 310 and the support portion 430 fasten to each other. At the same time, the support portion 430 communicates with the first hole portion 311.

[Base Unit 300 Rotates Around Central Axis 35c of Treatment Instrument Insertion Hole Portion 35a]

As described above, the base member 310 is attached to the support portion 430, the support portion 430 is attached to the body portion 410, and the body portion 410 is attached to the treatment instrument insertion cap 36.

In this state, as shown in FIG. 1C, the central axis direction of the treatment instrument insertion portion 35 is slanted relative to the direction of the central axis 33a of the grasping portion 33.

As shown in FIG. 1C, FIG. 5B, and FIG. 5C, an angle formed between the direction of the central axis 35c of the treatment instrument insertion hole portion 35a (the direction of the first central axis 311a of the first hole portion 311) and the direction of the central axis 33a of the grasping portion 33 is an angle θ1. The angle θ1 is invariable even if the advance and retreat assist tool 100 including the attachment portion 400 rotates around the central axis of the treatment instrument insertion cap 36.

As shown in FIG. 10 and FIG. 5B, an angle formed between the direction of the second central axis 313a and the direction of the central axis 33a of the grasping portion 33 is an angle θ2. The angle θ2 is an angle at which the advance and retreat assist tool 100 is slanted closer to the grasping portion 33, a clearance 60 between the grasping portion 33 and the rotary portion 700 is smallest, the distance between the grasping portion 33 and the rotary portion 700 is shortest, and the rotary portion 700 is adjacent to the grasping portion 33. Thus, the angle θ2 is an angle which is formed when the rotary portion 700 is operated to advance and retreat the treatment instrument 51 and which allows one hand to grasp the endoscope 10 and advance and retreat the treatment instrument 51 at the same time.

As shown in FIG. 10 and FIG. 5C, an angle formed between the direction of the second central axis 313a and the direction of the central axis 33a of the grasping portion 33 is an angle θ3. The angle θ3 is an angle at which the advance and retreat assist tool 100 is slanted away from the grasping portion 33, the clearance 60 between the grasping portion 33 and the rotary portion 700 is widest, and the distance between the grasping portion 33 and the rotary portion 700 is longest. Thus, the angle θ3 is an angle which is formed when the treatment instrument 51 does not need to be operated to advance and retreat and when the rotary portion 700 is not operated and which eliminates the interruption of the grasping by the advance and retreat assist tool 100.

As shown in FIG. 1C, FIG. 5B, and FIG. 5C, the attachment portion 400 attached to the treatment instrument insertion cap 36 rotates around the central axis 35c of the treatment instrument insertion hole portion 35a so that the angle θ1>the angle θ2 when the rotary portion 700 is operated and so that the angle θ3>the angle θ1 when the rotary portion 700 is not operated. As a result, the base member 310 attached to the attachment portion 400 also rotates.

[First Tubular Member 500]

As shown in FIG. 4A and FIG. 4B, the first tubular member 500 has the third central axis 500a. The first tubular member 500 is provided so that the third central axis 500a is provided along the direction of the second central axis 313a and so that the third central axis 500a is provided coaxially with the second central axis 313a. The first tubular member 500 is formed as a cylindrical member into which the treatment instrument 51 is inserted. The treatment instrument 51 is inserted into the first tubular member 500 from a proximal end portion 500c of the first tubular member 500, and is projected from a distal end portion 500b of the first tubular member 500.

As shown in FIG. 4A, the treatment instrument 51 is directly inserted into the first hole portion 311 when the first tubular member 500 advances. As shown in FIG. 4B, the treatment instrument 51 is inserted into the first hole portion 311 via the second hole portion 313 when the first tubular member 500 retreats. That is, the first tubular member 500 functions as a guide member which guides the treatment instrument 51 to the first hole portion 311.

As shown in FIG. 2B, FIG. 4A, and FIG. 4B, the first tubular member 500 has the above-mentioned third central axis 500a, and the distal end portion 500b which is inserted into the second hole portion 313 when the first tubular member 500 advances and which is removed from the second hole portion 313 when the first tubular member 500 retreats. The first tubular member 500 also has the proximal end portion 500c to which a proximal end portion 51b of the treatment instrument 51 is fixed by the fixing portion 600. The first tubular member 500 further has an opening portion 500d which is provided in the circumferential surface of the first tubular member 500 and with which a later-described protrusion portion 801 is engaged.

As shown in FIG. 4A, the distal end portion 500b is inserted into the second hole portion 313 so that the first tubular member 500 is in communication with the first hole portion 311 when the first tubular member 500 advances. As shown in FIG. 4B, the distal end portion 500b is removed from the second hole portion 313 so that the first tubular member 500 faces the first hole portion 311 when the first tubular member 500 retreats.

As shown in FIG. 4A, the opening portion 500d is provided on the side of the distal end portion 500b so that the opening portion 500d is not inserted into the second hole portion 313 when the distal end portion 500b is inserted into the second hole portion 313. The opening portion 500d is always exposed from the second hole portion 313. The opening portion 500d is, for example, circular. The opening portion 500d is a through-hole portion which passes through the first tubular member 500 in the thickness direction of the first tubular member 500. A pair of opening portions 500d are provided with respect to the third central axis 500a.

[Fixing Portion 600]

As shown in FIG. 2B, FIG. 3A, FIG. 3B, FIG. 4A, and FIG. 4B, the fixing portion 600 is provided at the proximal end portion 500c of the first tubular member 500. The fixing portion 600 fixes the proximal end portion 51b of the treatment instrument 51 to the proximal end portion 500c of the first tubular member 500. The fixing portion 600 has a cylindrical portion 601 through which the treatment instrument 51 is inserted and which is inserted into the proximal end portion 500c of the first tubular member 500, and a fixing member 605 which is mounted at the end portion of the cylindrical portion 601 and through which the treatment instrument 51 is inserted. The fixing portion 600 also has a fastening portion 603 which functions as a cap to cover the cylindrical portion 601 and the fixing member 605 and which fastens the cylindrical portion 601.

The fastening portion 603 rotates around the axis of the fastening portion 603 and thereby fastens the cylindrical portion 601, and compresses the fixing member 605 by fastening. The fixing member 605 comes into close contact with the proximal end portion 51b of the treatment instrument 51 by compression. As a result, the treatment instrument 51 becomes integral with the first tubular member 500 via the fixing portion 600. The fixing member 605 is formed by, for example, elastic rubber.

[Rotary Portion 700]

As shown in FIG. 1A and FIG. 1B, the rotary portion 700 rotates around the third central axis 500a. The rotary portion 700 is formed as a cylindrical member into which the first tubular member 500 is inserted. More specifically, the first tubular member 500 is inserted into the rotary portion 700 so that the central axis of the rotary portion 700 is provided coaxially with the third central axis 500a. As shown in FIG. 4A, the rotary portion 700 is rotatable around the second central axis 500a using the first tubular member 500 as a central axis while the first tubular member 500 is inserted in the rotary portion 700. As shown in FIG. 4A, the rotary portion 700 has a length such that the proximal end portion 500c of the first tubular member 500 projects outside the proximal end portion of the rotary portion 700 along the direction of the third central axis 500a when the distal end portion 500b of the first tubular member 500 is inserted in the second hole portion 313 while the first tubular member 500 is inserted in the rotary portion 700. As shown in FIG. 1A and FIG. 1B, the rotary portion 700 is provided adjacent to the grasping portion 33 when the advance and retreat assist tool 100 is attached to the endoscope 10. Thus, the rotary portion 700 functions as an operation knob.

As shown in FIG. 1A and FIG. 1B, the rotary portion 700 has recess portions 701 provided in the outer circumferential surface of the rotary portion 700. The recess portions 701 are provided along the direction of the third central axis 500a. The recess portions 701 are adjacent to each other in a direction around the third central axis 500a. The inner circumferential surface of the recess 701 is, for example, smoothly semicircular. As shown in FIG. 5, the recess portions 701 are formed as mounting surfaces to mount the fingers of the left hand grasping the grasping portion 33.

[Configuration of Advance and Retreat Mechanism 800]

The advance and retreat mechanism 800 intervenes between the rotary portion 700 and the first tubular member 500, the advance and retreat mechanism 800 converts the rotation force of the rotary portion 700 to an advance and retreat force of the first tubular member 500, and the advance and retreat mechanism 800 transmits the advance and retreat force to the first tubular member 500 and thereby advances and retreats the first tubular member 500 along the direction of the third central axis 500a, when the rotary portion 700 rotates.

As shown in FIG. 2B, FIG. 3A, FIG. 3B, FIG. 4A, and FIG. 4B, the advance and retreat mechanism 800 has the protrusion portion 801, the second tubular member 803, and a third tubular member 805. As shown in FIG. 4A and FIG. 4B, the protrusion portion 801, the second tubular member 803, and the third tubular member 805 intervene between the first tubular member 500 and the rotary portion 700 in the diametrical direction of the first tubular member 500.

[Protrusion Portion 801]

As shown in FIG. 3A, FIG. 3B, FIG. 3C, FIG. 4A, and FIG. 4B, the protrusion portion 801 is provided straight along the diametrical direction of the first tubular member 500 so that the protrusion portion 801 passes through a later-described long opening portion 803d and is inserted into a later-described spiral opening portion 805d. The protrusion portion 801 is engaged with the opening portion 500d, and is thereby engaged with the circumferential surface of the first tubular member 500. As shown in FIG. 3C, the protrusion portion 801 has a diameter such that the protrusion portion 801 abuts on the edge portion of the long opening portion 803d and the edge portion of the spiral opening portion 805d.

[Second Tubular Member 803]

As shown in FIG. 2B, FIG. 3A, FIG. 3B, FIG. 4A, and FIG. 4B, the second tubular member 803 has a fourth central axis 803a, and a distal end portion 803b which is fitted into and thus fixed to the second hole portion 313 so that the fourth central axis 803a is provided along the direction of the second central axis 313a and so that the fourth central axis 803a is provided coaxially with the second central axis 313a. The second tubular member 803 further has a proximal end portion 803c, and the long opening portion 803d provided in the circumferential surface of the second tubular member 803 along the direction of the fourth central axis 803a.

As shown in FIG. 4A and FIG. 4B, the distal end portion 803b is formed as a fixed end which is fixed to the base member 310 by, for example, a screw portion 213e when the distal end portion 803b is inserted in the second hole portion 313. The screw portion 213e is inserted through the side surface of the base member 310, and abuts on the circumferential surface of the distal end portion 803b.

As shown in FIG. 4A and FIG. 4B, the proximal end portion 803c is formed as a fixed end which is fixed to the support unit 950 by, for example, a screw portion 213f when the proximal end portion 803c is inserted in the fit hole portion 953c of the support unit 950. The screw portion 213f is inserted through the side surface of the support unit 950, and abuts on the circumferential surface of the proximal end portion 803c.

As a result, the second tubular member 803 is prevented from rotating and moving, and is fixed to the base unit 300 and the support unit 950.

As shown in FIG. 2B, the long opening portion 803d is provided straight from the side of the distal end portion 803b to the side of the proximal end portion 803c. As shown in FIG. 4A and FIG. 4B, the distal end portion of the long opening portion 803d is provided on the side of the distal end portion 803b so that the distal end portion of the long opening portion 803d is not inserted into the second hole portion 313 when the distal end portion 803b is inserted in the second hole portion 313. As shown in FIG. 4A and FIG. 4B, the proximal end portion of the long opening portion 803d is provided on the side of the proximal end portion 803c so that the proximal end portion of the long opening portion 803d is not inserted into the fit hole portion 953c of the support unit 950 when the proximal end portion 803c is inserted in the fit hole portion 953c of the support unit 950. That is, the long opening portion 803d is exposed from the second hole portion 313 and the fit hole portion 953c of the support unit 950.

As shown in FIG. 4A and FIG. 4B, the long opening portion 803d has a length slightly greater than the length from one edge portion of the later-described spiral opening portion 805d to the other edge portion in the direction of the fourth central axis 803a. One edge portion side of the long opening portion 803d faces one edge portion of the spiral opening portion 805d, and the other edge portion side of the long opening portion 803d faces the other edge portion of the spiral opening portion 805d. The long opening portion 803d is substantially equal in length to the rotary portion 700.

The length of the long opening portion 803d corresponds to the movement amount of the first tubular member 500, and corresponds to the advance and retreat amount of the treatment instrument 51. These are substantially equal in size to each other. The maximum value of the length corresponds to the maximum value of the movement amount and the maximum value of the advance and retreat amount.

Each of these maximum values corresponds to the size of the part to be treated with the treatment instrument 51, and has a desired value. The maximum value is, for example, 30 mm.

The long opening portion 803d does not pass through the second tubular member 803 in the direction of the fourth central axis 803a. The long opening portion 803d passes through the second tubular member 803 in the thickness direction of the second tubular member 803. A pair of long opening portions 803d are provided with respect to the fourth central axis 803a.

Such a second tubular member 803 is formed as a cylindrical member into which the first tubular member 500 is inserted so that part of the long opening portion 803d is in communication with the opening portion 500d and the protrusion portion 801 is inserted through the long opening portion 803d. The second tubular member 803 has a length such that the proximal end portion 500c of the first tubular member 500 projects outside the proximal end portion 803c of the second tubular member 803 along the direction of the second central axis 313a when the first tubular member 500 is inserted in the second tubular member 803, the distal end portion 500b of the first tubular member 500 is inserted in the second hole portion 313, and the distal end portion 803b of the second tubular member 803 is fitted in the second hole portion 313.

[Third Tubular Member 805]

As shown in FIG. 2B, the third tubular member 805 has a fifth central axis 805a provided coaxially with the third central axis 500a, and a distal end portion 805b. The third tubular member 805 also has a proximal end portion 805c, and the spiral opening portion 805d provided in the circumferential surface of the third tubular member 805 to wind around the fifth central axis 805a.

As shown in FIG. 4A and FIG. 4B, the third tubular member 805 is provided so that the distal end portion 805b is not inserted into the second hole portion 313 and the proximal end portion 805c is not inserted into the support unit 950.

As shown in FIG. 4A and FIG. 4B, the third tubular member 805 is inserted into the rotary portion 700 so that the third tubular member 805 rotates relative to the second tubular member 803 around the fifth central axis 805a together with the rotary portion 700. The third tubular member 805 is fixed to the rotary portion 700 by a screw portion 213g shown in FIG. 2B so that the third tubular member 805 rotates together with the rotary portion 700. Thus, the third tubular member 805 rotates in the same direction as the rotary portion 700. As shown in FIG. 3C, FIG. 4A, and FIG. 4B, the third tubular member 805 functions as a cylindrical member into which the second tubular member 803 is inserted so that part of the spiral opening portion 805d is in communication with part of the long opening portion 803d and so that the protrusion portion 801 inserted through the long opening portion 803d is inserted into the spiral opening portion 805d. Such a third tubular member 805 functions as a cam ring. The third tubular member 805 is substantially equal in length to the long opening portion 803d and the rotary portion 700.

As shown in FIG. 2B, the spiral opening portion 805d is provided from the distal end portion 805b to the proximal end portion 805c in the direction of the fifth central axis 805a. The spiral opening portion 805d does not pass through the third tubular member 805 in the direction of the fifth central axis 805a. The spiral opening portion 805d passes through the third tubular member 805 in the thickness direction of the third tubular member 805. A pair of spiral opening portions 805d are provided with respect to the third central axis 500a.

[Operation of Advance and Retreat Mechanism 800]

As shown in FIG. 1A, FIG. 1B, FIG. 3A, FIG. 3B, FIG. 3C, FIG. 4A, and FIG. 4B, if the rotary portion 700 rotates around the third central axis 500a, the third tubular member 805 also rotates simultaneously with the rotary portion 700. As a result, the spiral opening portion 805d provided in the third tubular member 805 also rotates.

As shown in FIG. 3A and FIG. 3B, the protrusion portion 801 is in abutment with the edge portion of the spiral opening portion 805d. Thus, in response to the rotation of the spiral opening portion 805d, the protrusion portion 801 is pressed to rotate by the spiral opening portion 805d. As shown in FIG. 3A and FIG. 3B, the protrusion portion 801 is inserted through the long opening portion 803d, and is also in abutment with the edge portion of the long opening portion 803d. Thus, the protrusion portion 801 is pressed to rotate by the spiral opening portion 805d, so that the protrusion portion 801 moves in the long opening portion 803d along the direction of the third central axis 500a.

Thus, the third tubular member 805 rotates together with the rotation of the rotary portion 700, so that the spiral opening portion 805d rotates. As a result of the rotation of the spiral opening portion 805d, the protrusion portion 801 moves in the long opening portion 803d along the direction of the third central axis 500a by the spiral opening portion 805d.

The protrusion portion 801 abuts on the edge portion of the long opening portion 803d, so that the first tubular member 500 having the distal end portion 500b with which the protrusion portion 801 is engaged is prevented from rotating around the third central axis 500a.

The spiral opening portion 805d rotates, and the protrusion portion 801 moves in the long opening portion 803d along the direction of the third central axis 500a, so that the first tubular member 500 having the distal end portion 500b with which the protrusion portion 801 is engaged advances and retreats along the direction of the third central axis 500a while the rotation of the first tubular member 500 around the third central axis 500a is prevented. As a result, the treatment instrument 51 fixed to the first tubular member 500 advances and retreats.

The distal end portion 803b of the second tubular member 803 is fitted into and thus fixed to the second hole portion 313, and the proximal end portion 803c of the second tubular member 803 is fitted into and thus fixed to the fit hole portion 953c of the support unit 950. Therefore, the second tubular member 803 remains fixed. This prevents the long opening portion 803d from rotating in the same manner as the spiral opening portion 805d.

The protrusion portion 801 only moves in the long opening portion 803d along the direction of the third central axis 500a. Therefore, the first tubular member 500 only advances and retreats along the direction of the third central axis 500a, and the rotation of the first tubular member 500 around the third central axis 500a is prevented. Similarly, the treatment instrument 51 only advances and retreats, and the rotation of the treatment instrument 51 around the third central axis 500a is prevented.

Thus, the advance and retreat mechanism 800 advances and retreats the treatment instrument 51 while the treatment instrument 51 is prevented from rotating around the third central axis 500a in response to the rotation of the rotary portion 700 around the third central axis 500a when the rotary portion 700 rotates around the third central axis 500a.

[Regulating Mechanism 900]

The regulating mechanism 900 regulates the advance and retreat of the first tubular member 500 when the first tubular member 500 advances and retreats along the direction of the third central axis 500a so that the distal end portion 500b of the first tubular member 500 moves along the direction of the third central axis 500a between a part where the first hole portion 311 provided on the distal end portion side of the rotary portion 700 is in communication with the second hole portion 313 and a position on the side where the first tubular member 500 provided on the proximal end portion side of the rotary portion 700 comes off the rotary portion 700.

The regulating mechanism 900 is formed by the protrusion portion 801 and by the edge portion of the spiral opening portion 805d.

[Support Unit 950]

As shown in FIG. 1A, FIG. 1B, FIG. 2A, FIG. 2B, FIG. 3A, FIG. 3B, FIG. 4A, and FIG. 4B, the support unit 950 supports the first tubular member 500 via the protrusion portion 801, the second tubular member 803, and the third tubular member 805 so that the third central axis 500a is provided coaxially with the second central axis 313a, the first tubular member 500 advances and retreats along the direction of the third central axis 500a, and thus the first tubular member 500 is prevented from moving in a direction that intersects at right angles with the direction of the third central axis 500a.

The support unit 950 has a base member 951 which is provided along the direction of the third central axis 500a and which is provided on the side of the rotary portion 700, and a base member 953 which is provided along the direction that intersects at right angles with the direction of the third central axis 500a and which is provided above the rotary portion 700.

The base member 951 has one end portion fixed to the base member 310 by, for example, a screw portion 213h, and the other end portion fixed to the base member 953 by, for example, a screw portion 213i.

The base member 953 has the fit hole portion 953c into which the proximal end portion 803c of the second tubular member 803 is fitted. The base member 953 is fixed, by, for example, the screw portion 213f, to the proximal end portion 803c of the second tubular member 803 which is fitted into the fit hole portion 953c.

The support unit 950 supports the first tubular member 500 via the base member 310 and the second tubular member 803. The support unit 950 supports the third tubular member 805 via the base member 310, the second tubular member 803, and a washer 955.

[Functions]

[Attachment of Advance and Retreat Assist Tool 100 to Endoscope 10]

As shown in FIG. 1A, FIG. 1B, FIG. 4A, and FIG. 4B, the fixing unit 400 fixes the base unit 300 to the endoscope 10 so that the first hole portion 311 faces the treatment instrument insertion hole portion 35a.

At the same time, as has been described in [Attachment of Body Portion 410 to Treatment Instrument Insertion Cap 36], the body portion 410 is pressed into the proximal end portion of the treatment instrument insertion cap 36 from the side surface of the treatment instrument insertion portion 35 via the cutout portion 413 in the diametrical direction of the body portion 410 as shown in FIG. 2C, FIG. 4A, and FIG. 4B, and is thereby attached to the proximal end portion of the treatment instrument insertion cap 36.

As has been described in [Attachment of Support Portion 430 to Base Member 310], the support portion 430 is then screwed into the third hole portion 315 in the central axis direction of the attachment portion 400 as shown in FIG. 2C, FIG. 4A, and FIG. 4B so that the base thread groove portion 315a and the proximal support thread groove portion 437 mesh with each other, and the support portion 430 is thereby attached to the base member 310. Thus, the base member 310 is fastened to the support portion 430.

As has been described in [Attachment of Body Portion 410 and Support Portion 430], the support portion 430 is then screwed into the body thread groove portion 411 in the central axis direction of the attachment portion 400 as shown in FIG. 2C, FIG. 4A, and FIG. 4B so that the body thread groove portion 411 and the distal end support thread groove portion 431 mesh with each other, and the support portion 430 is thereby attached to the body portion 410. Thus, the body portion 410 is fastened to the support portion 430.

In the attachment described above, the order of attachment is not specifically limited. Consequently, the advance and retreat assist tool 100 is attached to the treatment instrument insertion cap 36.

As shown in FIG. 1A, FIG. 1B, FIG. 1C, FIG. 5A, and FIG. 5B, the body portion 410 rotates around the central axis 35c of the treatment instrument insertion hole portion 35a after the body portion 410 and the support portion 430 have temporarily unfastened from each other so that, for example, the angle θ1>the angle θ2. The body portion 410 and the support portion 430 then fasten to each other again. As a result, the angle θ1>the angle θ2. As shown in FIG. 1A and FIG. 1B, when the advance and retreat assist tool 100 is attached to the endoscope 10, the rotary portion 700 is slanted toward the central axis 33a of the grasping portion 33 relative to the central axis 35c of the treatment instrument insertion hole portion 35a. The rotary portion 700 is then provided adjacent to the grasping portion 33.

[Provision of Treatment Instrument 51]

After the insertion portion 20 of the endoscope 10 is inserted into the body cavity, the treatment instrument 51 is inserted from the fixing portion 600, and inserted through the first tubular member 500, as shown in FIG. 1A and FIG. 1B. The treatment instrument 51 is further inserted into the endoscope 10 from the treatment instrument insertion portion 35. As shown in FIG. 1A and FIG. 1B, the distal end portion 51a of the treatment instrument 51 then projects from the distal opening portion 35b. The length of the projecting distal end portion 51a of the treatment instrument 51 is a desired length.

The fastening portion 603 rotates around the axis of the fastening portion 603 and thereby fastens the cylindrical portion 601, and compresses the fixing member 605 by fastening. The fixing member 605 comes into close contact with the proximal end portion 51b of the treatment instrument 51 by compression. As a result, the treatment instrument 51 is fixed to the advance and retreat assist tool 100 via the fixing portion 600 and the first tubular member 500.

[Grasping of Endoscope 10 and Treatment Instrument 51]

As shown in FIG. 5A, the grasping portion 33 is grasped by the left hand of the surgeon, the rotary portion 700 adjacent to the grasping portion 33 is operated by, for example, the little finger or third finger of the left hand, and the bending operation portion is operated by the thumb of the left hand. In this instance, as shown in FIG. 5B, the angle θ1>the angle θ2, so that the clearance 60 between the grasping portion 33 and the rotary portion 700 is smallest, the distance between the grasping portion 33 and the rotary portion 700 is shortest, and the rotary portion 700 is provided adjacent to the grasping portion 33. The endoscope 10 is grasped and the treatment instrument 51 is operated to advance and retreat with one hand at the same time.

[Advance Operation of Treatment Instrument 51]

When the rotary portion 700 is operated by, for example, the little finger or third finger of the left hand, the rotary portion 700 rotates in one direction around the third central axis 500a. At the same time, the third tubular member 805 also rotates in the same manner as the rotary portion 700. As a result, the spiral opening portion 805d provided in the third tubular member 805 also rotates.

As a result of the rotation of the spiral opening portion 805d, the protrusion portion 801 moves in the long opening portion 803d along the direction of the third central axis 500a by the spiral opening portion 805d.

The first tubular member 500 having the distal end portion 500b with which the protrusion portion 801 is engaged advances along the direction of the third central axis 500a. As a result, the treatment instrument 51 fixed to the first tubular member 500 advances.

Since the second tubular member 803 is fixed, the long opening portion 803d is fixed, so that the long opening portion 803d is prevented from rotating in the same manner as the spiral opening portion 805d. Therefore, the protrusion portion 801 only moves in the long opening portion 803d along the direction of the third central axis 500a. Therefore, the first tubular member 500 only advances along the direction of the third central axis 500a, and the rotation of the first tubular member 500 around the third central axis 500a is prevented. Similarly, the treatment instrument 51 only advances, and the rotation of the treatment instrument 51 around the third central axis 500a is prevented.

The protrusion portion 801 abuts on one edge portion of the spiral opening portion 805d, so that the advance of the first tubular member 500 is stopped, and the advance of the treatment instrument 51 is stopped.

[Retreat Operation of Treatment Instrument 51]

When the rotary portion 700 is operated by, for example, the little finger or third finger of the left hand, the rotary portion 700 rotates in the other direction around the third central axis 500a. At the same time, the third tubular member 805 also rotates in the same manner as the rotary portion 700. As a result, the spiral opening portion 805d provided in the third tubular member 805 also rotates.

As a result of the rotation of the spiral opening portion 805d, the protrusion portion 801 moves in the long opening portion 803d along the direction of the third central axis 500a by the spiral opening portion 805d.

The first tubular member 500 having the distal end portion 500b with which the protrusion portion 801 is engaged retreats along the direction of the third central axis 500a. As a result, the treatment instrument 51 fixed to the first tubular member 500 retreats.

Since the second tubular member 803 is fixed, the long opening portion 803d is fixed, so that the long opening portion 803d is prevented from rotating in the same manner as the spiral opening portion 805d. Therefore, the protrusion portion 801 only moves in the long opening portion 803d along the direction of the third central axis 500a. Therefore, the first tubular member 500 only retreats along the direction of the third central axis 500a, and the rotation of the first tubular member 500 around the third central axis 500a is prevented. Similarly, the treatment instrument 51 only retreats, and the rotation of the treatment instrument 51 around the third central axis 500a is prevented.

The protrusion portion 801 abuts on the other edge portion of the spiral opening portion 805d, so that the retreat of the first tubular member 500 is stopped, and the retreat of the treatment instrument 51 is stopped. This also prevents the first tubular member 500 from coming off the rotary portion 700.

[When Advance and Retreat Operations of Treatment Instrument 51 are not Needed]

As shown in FIG. 10 and FIG. 5C, the attachment portion 400 attached to the treatment instrument insertion cap 36 rotates around the central axis 35c of the treatment instrument insertion hole portion 35a so that the angle θ3>the angle θ1. As a result, the advance and retreat assist tool 100 including the attachment portion 400 also rotates. As shown in FIG. 1C and FIG. 5C, the angle θ3>the angle θ1, so that the advance and retreat assist tool 100 is slanted away from the grasping portion 33, the clearance 60 between the grasping portion 33 and the rotary portion 700 is widest, and the distance between the grasping portion 33 and the rotary portion 700 is longest. The interruption of the grasping by the advance and retreat assist tool 100 is eliminated.

The attachment portion 400 rotates as described above after the treatment instrument 51 is removed from the endoscope 10.

The attachment portion 400 also rotates as described above after the body portion 410 and the support portion 430 have temporarily unfastened from each other. The body portion 410 and the support portion 430 will then fasten to each other again.

When the attachment portion 400 rotates, rotational resistance applied to the inner circumferential surface of the distal end portion of the body portion 410 by the edge portion of the treatment instrument insertion cap 36 is reduced by the cutout portion 413.

[Advantageous Effects]

Thus, according to the present embodiment, the second central axis 313a (the third central axis 500a) is slanted relative to the first central axis 311a. The attachment portion 400 attaches the base unit 300 to the treatment instrument insertion portion 35 so that the base unit 300 is rotatable around the central axis 35c of the treatment instrument insertion hole portion 35a.

As a result, according to the present embodiment, as shown in FIG. 1A, FIG. 1B, FIG. 1C, FIG. 5A, and FIG. 5B, the advance and retreat assist tool 100 is slanted closer to the grasping portion 33, and the clearance 60 between the grasping portion 33 and the rotary portion 700 can be smallest. Thus, according to the present embodiment, the fingers of the hand grasping the grasping portion 33 reach the rotary portion 700 without fail, the surgeon is not burdened, the operation is easier, and the endoscope 10 can be grasped and the treatment instrument 51 can be operated to advance and retreat with one hand at the same time. Moreover, according to the present embodiment, it is possible to prevent the whole endoscope 10 from increasing in size without interrupting one-handed advance and retreat operations.

According to the present embodiment, as shown in FIG. 1C and FIG. 5C, the advance and retreat assist tool 100 is slanted away from the grasping portion 33, and the clearance 60 between the grasping portion 33 and the rotary portion 700 can be widest. Thus, according to the present embodiment, when the treatment instrument 51 is not advanced and retreated, the interruption of the grasping by the advance and retreat assist tool 100 is eliminated.

As described above, the present embodiment enables simple one-handed operations and smooth one-handed advance and retreat operations, and enables the advance and retreat assist tool 100 to rotate around the central axis 35c of the treatment instrument insertion hole portion 35a in accordance with procedures.

According to the present embodiment, as shown in FIG. 1A, FIG. 1B, FIG. 10, FIG. 5A, and FIG. 5B, the angle θ1>the angle θ2, so that the rotary portion 700 can be provided adjacent to the grasping portion 33. Thus, the present embodiment ensures that the fingers of the hand grasping the grasping portion 33 can reach the rotary portion 700 and that the treatment instrument 51 can be advanced and retreated while the grasping portion 33 is grasped. According to the present embodiment, the surgeon can grasp the endoscope 10 and advance and retreat the treatment instrument 51 with one hand. According to the present embodiment, it is possible to prevent the endoscope 10 from increasing in size.

According to the present embodiment, as shown in FIG. 10 and FIG. 5C, the angle θ3>the angle θ1, so that the interruption of the grasping by the advance and retreat assist tool 100 can be eliminated when the treatment instrument 51 is not advanced and retreated.

According to the present embodiment, the bending operation portion 37 and the switch portion 39 are provided in the grasping portion 33. Thus, according to the present embodiment, the surgeon can operate the bending operation portion 37 and the switch portion 39 while grasping the endoscope 10 and advancing and retreating the treatment instrument 51 with one hand at the same time.

According to the present embodiment, as shown in FIG. 2C, FIG. 4A, and FIG. 4B, the support portion 430 is screwed into the body portion 410 attached to the treatment instrument insertion cap 36. The support portion 430 then presses the edge portion of the treatment instrument insertion hole portion 35a into the body portion 410, and the attachment portion 400 is fixed to the treatment instrument insertion portion 35. As a result, according to the present embodiment, the fixing of the advance and retreat assist tool 100 to the endoscope 10 can be ensured, and the advance and retreat assist tool 100 can be easily separated from the endoscope 10. According to the present embodiment, the attachment portion 400 can be easily disassembled and more efficiently cleaned.

According to the present embodiment, as shown in FIG. 2C, FIG. 4A, and FIG. 4B, the interference prevention member 450 can prevent the support portion 430 and the treatment instrument insertion cap 36 from damaging each other. Since the support portion 430 and the treatment instrument insertion cap 36 are in close contact with each other via the interference prevention member 450, the interference prevention member 450 can also keep the support portion 430 and the treatment instrument insertion cap 36 watertight.

According to the present embodiment, as shown in FIG. 2C, FIG. 4A, and FIG. 4B, the advance and retreat assist tool 100 can be easily attached to the treatment instrument insertion cap 36, owing to the presence of cutout portion 413. According to the present embodiment, the distal end portion of the body portion 410 formed as the inner flange can be caught on the edge portion 36c of the treatment instrument insertion cap 36 formed as the outer flange due to the cutout portion 413. As a result, according to the present embodiment, the support portion 430 can press the edge portion 36c into the body portion 410, as described above. Thus, according to the present embodiment, it is possible to prevent the body portion 410 from coming off the treatment instrument insertion cap 36. According to the present embodiment, rotational resistance can be reduced by the cutout portion 413 when the body portion 410 rotates.

According to the present embodiment, the second central axis 313a (the third central axis 500a) is slanted relative to the first central axis 311a, and the rotary portion 700 rotates around the third central axis 500a. The advance and retreat mechanism 800 converts the rotation force of the rotary portion 700 to an advance and retreat force, and advances and retreats the first tubular member 500 by the advance and retreat force. Thus, according to the present embodiment, it is possible to prevent a size increase of the endoscope 10, ensure that the treatment instrument 51 is finely advanced and retreated by one hand grasping the grasping portion 33, and avoid a burden being placed on the surgeon.

More specifically, according to the present embodiment, in the advance and retreat mechanism 800, the rotation force of the rotary portion 700 is not transmitted directly to the first tubular member 500, converted to an advance and retreat force by the second tubular member 803 and the third tubular member 805, and transmitted indirectly to the first tubular member 500. Thus, according to the present embodiment, it is possible to prevent the treatment instrument 51 from rapidly advancing and retreating, and finely advance and retreat the treatment instrument 51.

According to the present embodiment, the treatment instrument 51 can be advanced and retreated by the advance and retreat mechanism 800 without rotating together with the rotary portion 700.

According to the present embodiment, the protrusion portion 801 abuts on the edge portion of the spiral opening portion 805d, so that the advance and retreat of the first tubular member 500 can be regulated, and the advance and retreat of the treatment instrument 51 can be regulated.

The long opening portion 803d may have a length slightly smaller than the length from one edge portion of the spiral opening portion 805d to the other edge portion in the direction of the fourth central axis 803a. In this case, the protrusion portion 801 abuts on the edge portion of the long opening portion 803d, so that the advance and retreat of the first tubular member 500 can be regulated, and the advance and retreat of the treatment instrument 51 can be regulated. The regulating mechanism 900 is then formed by the protrusion portion 801 and by the edge portion of the long opening portion 803d.

The long opening portion 803d may have a length substantially equal to the length from one edge portion of the spiral opening portion 805d to the other edge portion in the direction of the fourth central axis 803a. In this case, one edge portion of the long opening portion 803d faces one edge portion of the spiral opening portion 805d, and the other edge portion of the long opening portion 803d faces the other edge portion of the spiral opening portion 805d. In this case, the protrusion portion 801 abuts on the edge portion of the long opening portion 803d and the edge portion of the spiral opening portion 805d, so that the advance and retreat of the first tubular member 500 can be regulated, and the advance and retreat of the treatment instrument 51 can be regulated. The regulating mechanism 900 is then formed by the protrusion portion 801, the edge portion of the long opening portion 803d, and the edge portion of the spiral opening portion 805d.

Thus, the regulating mechanism 900 has only to be formed by the protrusion portion 801 and at least one of the end portion of the spiral opening portion 805d and the edge portion of the long opening portion 803d.

According to the present embodiment, the support unit 950 can prevent the first tubular member 500 from moving in a direction that intersects at right angles with the direction of the third central axis 500a. Thus, according to the present embodiment, the first tubular member 500 and the treatment instrument 51 can be advanced and retreated.

According to the present embodiment, it is possible to freely adjust the advance and retreat amount of the treatment instrument 51 by setting the length of the long opening portion 803d and the length of the spiral opening portion 805d to desired lengths.

According to the present embodiment, for example, the first tubular member 500 may have an unshown index which is provided on the outer circumferential surface of the first tubular member 500 and which indicates the advance and retreat position of the treatment instrument 51. When the first tubular member 500 is exposed from the rotary portion 700 in accordance with the advance and retreat, the index portion is exposed from the rotary portion 700. Thus, the surgeon can know the advance and retreat position of the treatment instrument 51 by checking the index portion.

[First Modification]

Figure 6B:
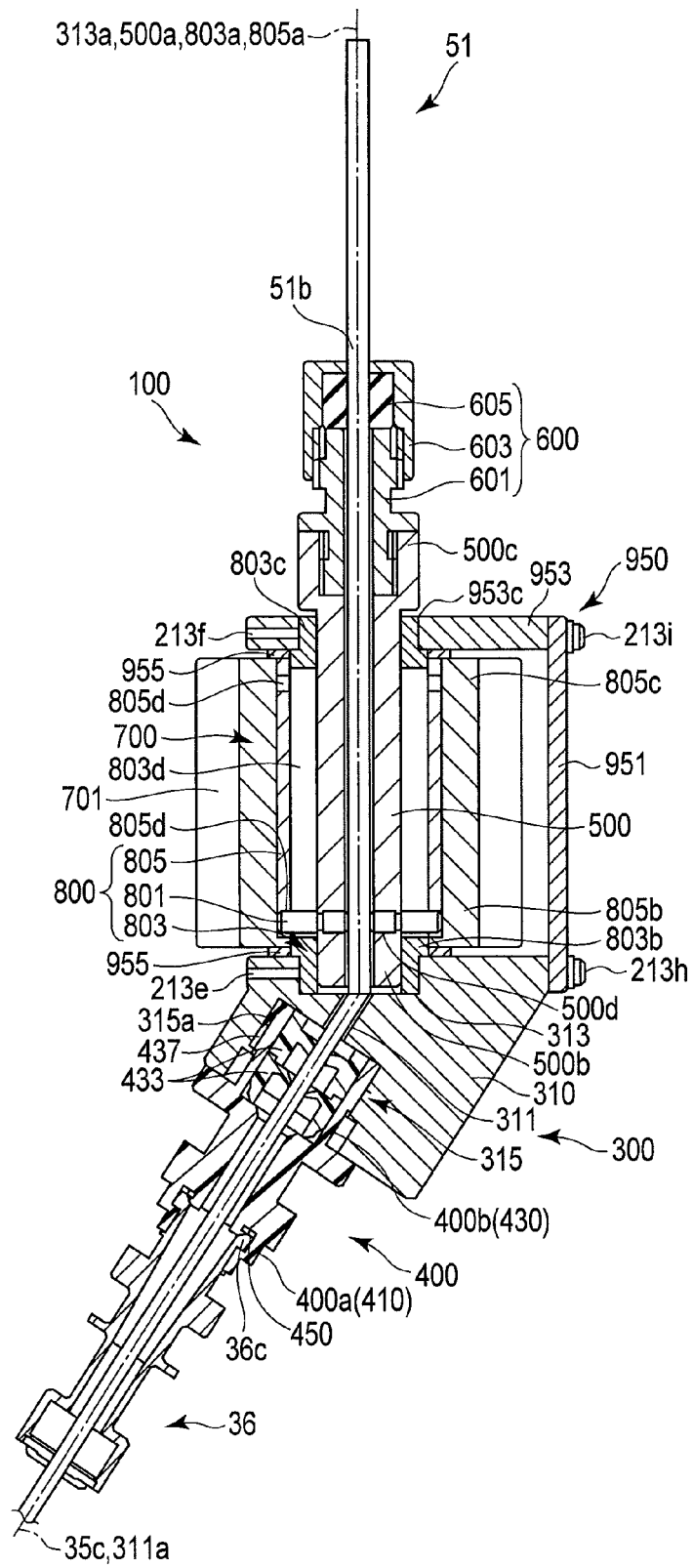
FIG. 6B is a sectional view of the advance and retreat assist tool shown in FIG. 6A.
Figure 6C:
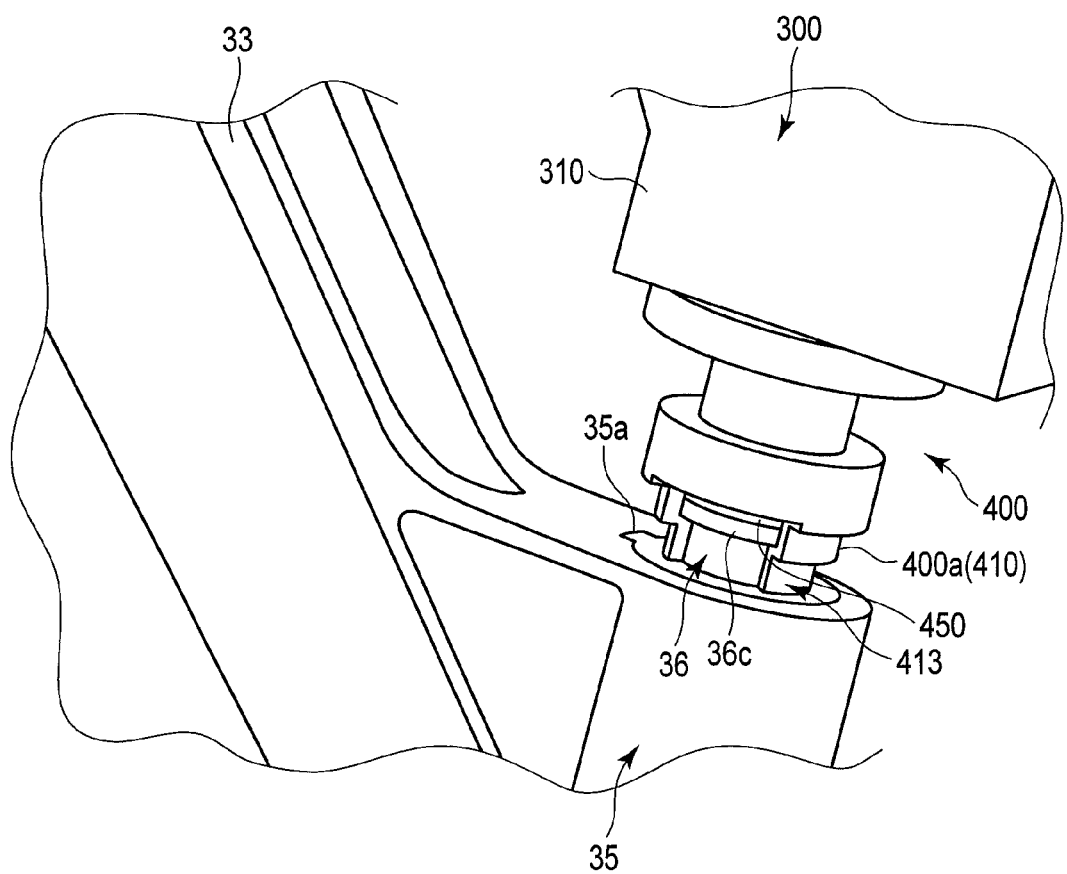
FIG. 6C is an enlarged perspective view around the treatment instrument insertion cap in which the advance and retreat assist tool shown in FIG. 6A is attached to the treatment instrument insertion cap.

A first modification of the first embodiment is now described with reference to FIG. 6A, FIG. 6B, and FIG. 6C. In the present modification, components different from the above components alone are described below.

[Configuration]

In the present modification, the body portion 410 and the support portion 430 are integrated in the attachment portion 400. Thus, the attachment portion 400 has a distal end portion 400a functioning as the body portion 410, and a proximal end portion 400b functioning as the support portion 430. The distal end portion 400a of the attachment portion 400 has the cutout portion 413.

[Advantageous Effects]

According to the present modification, the advance and retreat assist tool 100 can be easily fixed to the endoscope 10, and the advance and retreat assist tool 100 can be quickly separated from the endoscope 10. According to the present modification, the advance and retreat assist tool 100 can be easily rotated. According to the present modification, the body thread groove portion 411 and the distal end support thread groove portion 431 are obviated, and the configuration of the attachment portion 400 can be simpler. The present modification is best suited to a disposable attachment portion 400.

[Second Modification]

Figure 7A:
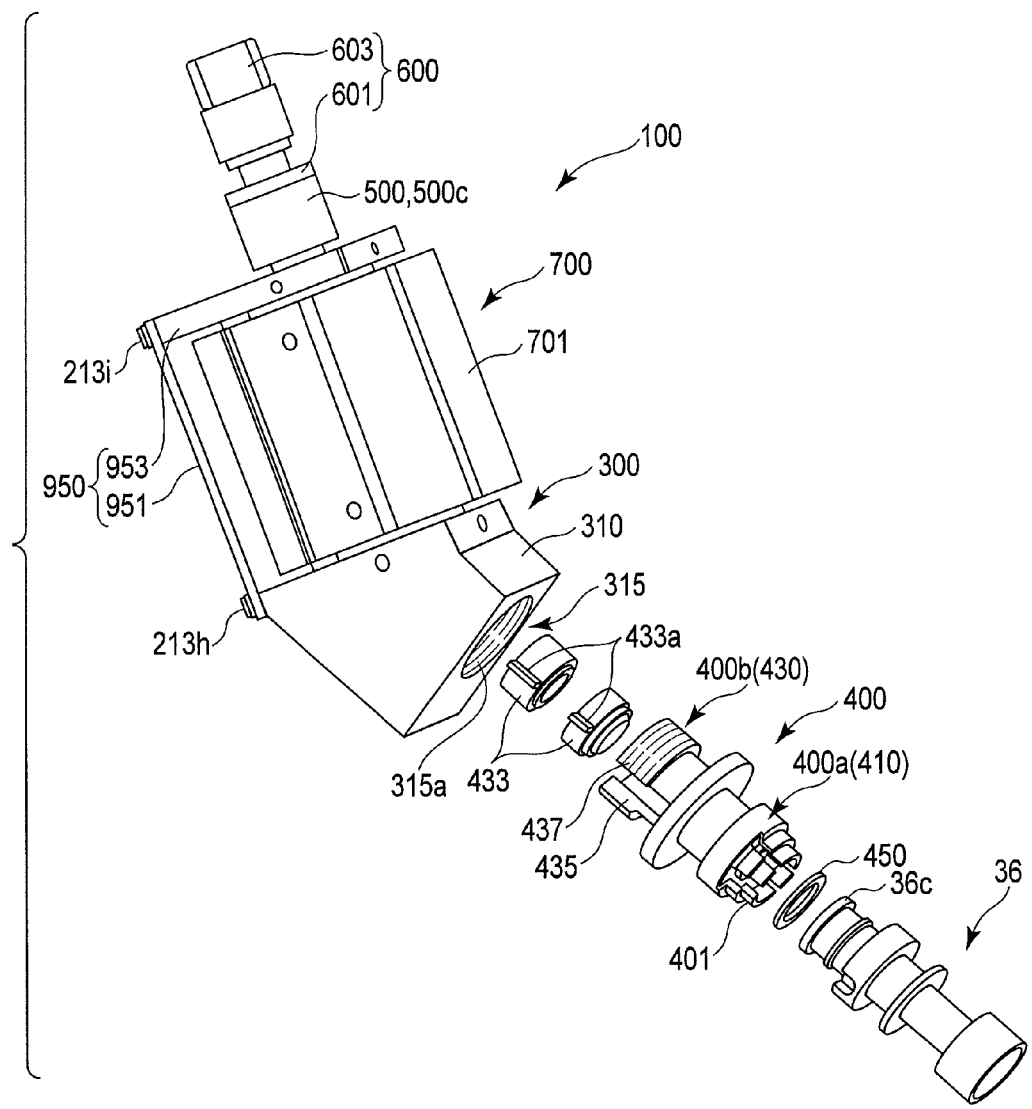
FIG. 7A is an exploded perspective view of mainly the attachment portion according to a second modification of the first embodiment.
Figure 7B:
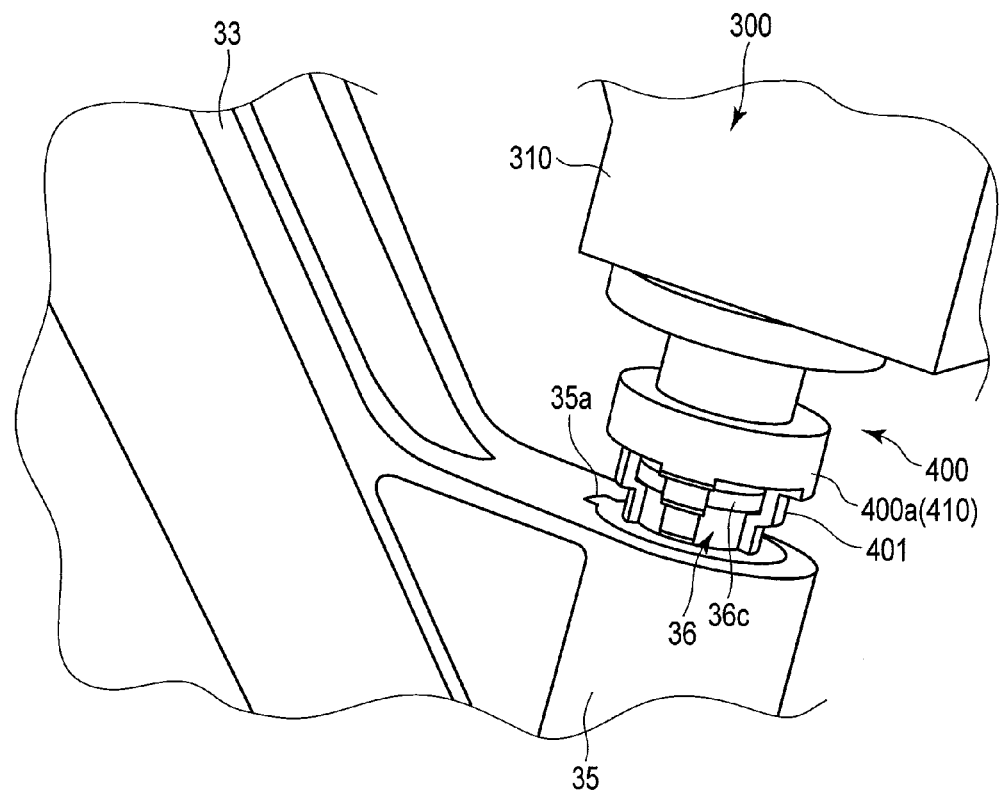
FIG. 7B is an enlarged perspective view around the treatment instrument insertion cap in which the advance and retreat assist tool shown in FIG. 7A is attached to the treatment instrument insertion cap.

A second modification of the first embodiment is now described with reference to FIG. 7A and FIG. 7B. In the present modification, components different from the above components alone are described below.

[Configuration]

The distal end portion 400a of the attachment portion 400 has claw portions 401 which extend along the central axis direction of the attachment portion 400 and then bend inward toward the central axis of the attachment portion 400. The claw portions 401 are equally spaced out in the circumferential direction of the attachment portion 400.

In this case, the claw portions 401 are elastically deformed to expand outward, and the end face of the distal end portion 400a of the attachment portion 400 abuts on the end face of the edge portion 36c of the treatment instrument insertion cap 36 in the central axis direction of the attachment portion 400. The distal end portion 400a of the attachment portion 400 is then attached to the treatment instrument insertion portion 35 when the claw portions 401 are closed and thus caught on the edge portion 36c.

[Advantageous Effects]

According to the present modification, the advance and retreat assist tool 100 can be easily fixed to the endoscope 10, and the advance and retreat assist tool 100 can be quickly separated from the endoscope 10. According to the present modification, the advance and retreat assist tool 100 can be easily rotated. According to the present modification, the body thread groove portion 411 and the distal end support thread groove portion 431 are obviated, and the configuration of the attachment portion 400 can be simpler. The present modification is best suited to a disposable attachment portion 400.

[Third Modification]

Figure 8:
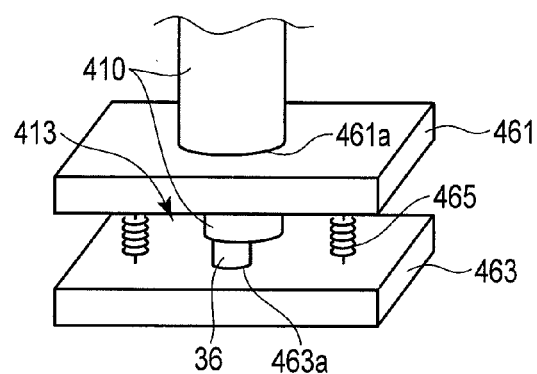
FIG. 8 is an enlarged perspective view around the treatment instrument insertion cap according to a third modification of the first embodiment.

A third modification of the first embodiment is now described with reference to FIG. 8. In the present modification, components different from the above components alone are described below.

[Configuration]

The advance and retreat assist tool 100 has a body support portion 461 which supports the distal end portion of the body portion 410, and an insertion support portion 463 which supports the proximal end portion of the treatment instrument insertion cap 36. The advance and retreat assist tool 100 further has an urging portion 465 which is connected to the body support portion 461 and the insertion support portion 463 and which urges at least one of the distal end portion of the body portion 410 via the body support portion 461 and the proximal end portion of the treatment instrument insertion cap 36 via the insertion support portion 463 toward the other.

The body support portion 461 is formed by, for example, a plate-shaped material. The body support portion 461 has an engagement hole portion 461a with which the distal end portion engages. When the distal end portion of the body portion 410 engages with the engagement hole portion 461a, the body support portion 461 supports the distal end portion of the body portion 410. The body support portion 461 may be formed by a pair of plate materials, and the plate materials catch the distal end portion of the body portion 410 from both sides to support the distal end portion of the body portion 410. How the body support portion 461 provides support is not specifically limited as long as the body support portion 461 can support the distal end portion of the body portion 410.

The same also applies to the insertion support portion 463.

The urging portion 465 has, for example, a helical spring. The proximal end portion of the urging portion 465 is fixed to the body support portion 461, and the distal end portion of the urging portion 465 is fixed to the insertion support portion 463. The urging portion 465 is provided along the direction of the central axis 35c of the treatment instrument insertion hole portion 35a, and provides an urging force along the direction of the central axis 35c. The urging portion 465 may be provided on both sides of the central axis 35c (the distal end portion of the body portion 410 and the proximal end portion of the treatment instrument insertion cap 36). Alternatively, although not shown, the urging portion 465 may be spirally provided around the distal end portion of the body portion 410 and the proximal end portion of the treatment instrument insertion cap 36.

[Advantageous Effects]

According to the present modification, when the advance and retreat assist tool 100 is fixed to the endoscope 10, the fixing can be reinforced. The present modification can be incorporated into the first and second modifications. In this case, the body support portion 461 functions as a distal end support portion which supports the distal end portion of the attachment portion 400.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An advance and retreat assist tool for an endoscopic treatment instrument, the advance and retreat assist tool comprising:
    a base unit comprising a first hole portion which has a first central axis and a second hole portion which has a second central axis slanted relative to the first central axis and which is in communication with the first hole portion;
    an attachment portion which attaches the base unit to a treatment instrument insertion portion provided in a grasping portion of an endoscope so that a side of the first hole portion having the first central axis faces a treatment instrument insertion hole portion and so that the base unit is rotatable around a central axis of the treatment instrument insertion hole portion;
    a first tubular member provided to have a third central axis which is provided along a direction of the second central axis and is provided coaxially with the second central axis, the endoscopic treatment instrument being inserted into and fixed to the first tubular member;
    a rotary portion into which the first tubular member is inserted and which rotates around the third central axis of the first tubular member; and
    an advance and retreat mechanism which converts a rotation force of the rotary portion to an advance and retreat force along a direction of the third central axis of the first tubular member to advance and retreat the first tubular member and endoscopic treatment instrument when the rotary portion rotates while preventing rotation of the first tubular member.

2. The advance and retreat assist tool for the endoscopic treatment instrument according to claim 1, wherein
    a central axis direction of the treatment instrument insertion hole portion is slanted relative to a central axis direction of the grasping portion, and
    the attachment portion rotates around the central axis of the treatment instrument insertion hole portion so that an angle θ1>an angle θ2 when the rotary portion is rotated and so that an angle θ3>the angle θ1 when the endoscopic treatment instrument does not need to be advanced and retreated and when the rotary portion is not operated,
    an angle formed between the central axis direction of the treatment instrument insertion hole portion and the central axis direction of the grasping portion being the angle θ1,
    an angle formed between the direction of the second central axis and the central axis direction of the grasping portion when the rotary portion is operated being the angle θ2,
    an angle formed between the direction of the second central axis and the central axis direction of the grasping portion when the endoscopic treatment instrument does not need to be advanced and retreated and when the rotary portion is not operated being the angle θ3.

3. The advance and retreat assist tool for the endoscopic treatment instrument according to claim 2, wherein the attachment portion comprises
    a cylindrical body portion which is removably attached to the treatment instrument insertion portion so that the body portion is rotatable around the central axis of the treatment instrument insertion hole portion, and
    a cylindrical support portion which supports the base unit so that the first central axis is provided coaxially with the central axis of the treatment instrument insertion hole portion and so that the first hole portion faces the treatment instrument insertion hole portion.

4. The advance and retreat assist tool for the endoscopic treatment instrument according to claim 3, wherein
    the support portion is removably attached to the body portion, and
    while the body portion is attached to the treatment instrument insertion portion, the support portion is screwed into the body portion, and the support portion is thereby attached to the body portion.

5. The advance and retreat assist tool for the endoscopic treatment instrument according to claim 4, wherein
    when the support portion is attached to the body portion, an edge portion of the treatment instrument insertion hole portion is provided between the support portion and the body portion in the central axis direction of the treatment instrument insertion hole portion, and
    the support portion is attached to the body portion so that the support portion presses the edge portion of the treatment instrument insertion hole portion into the body portion, and the attachment portion is fixed to the treatment instrument insertion portion.

6. The advance and retreat assist tool for the endoscopic treatment instrument according to claim 5, further comprising
    an interference prevention member which intervenes between the support portion and the edge portion of the treatment instrument insertion hole portion in the central axis direction of the treatment instrument insertion hole portion and which prevents interference between the support portion and the edge portion of the treatment instrument insertion hole portion.

7. The advance and retreat assist tool for the endoscopic treatment instrument according to claim 5, wherein
    the body portion has a cutout portion which is formed by a depression of a part of an edge portion of the body portion in a central axis direction of the body portion, and
    the body portion is pressed into the treatment instrument insertion portion from a side surface of the treatment instrument insertion portion via the cutout portion in a diametrical direction of the body portion, and is thereby attached to the treatment instrument insertion portion.

8. The advance and retreat assist tool for the endoscopic treatment instrument according to claim 7, further comprising:
    a distal end support portion which supports a distal end portion of the body portion;
    an insertion support portion which supports the treatment instrument insertion portion; and
    an urging portion which is connected to the distal end support portion and the insertion support portion and which urges at least one of the distal end portion of the attachment portion via the distal end support portion and the treatment instrument insertion portion via the insertion support portion toward the other.

9. The advance and retreat assist tool for the endoscopic treatment instrument according to claim 2, wherein the attachment portion comprises
a distal end portion which is attached to the treatment instrument insertion portion so that the distal end portion of the attachment portion is removably attached to the treatment instrument insertion portion and is also rotatable around the central axis of the treatment instrument insertion hole portion, and
a proximal end portion which is removably attached to the base unit and also supports the base unit.

10. The advance and retreat assist tool for the endoscopic treatment instrument according to claim 9, further comprising
an interference prevention member which intervenes between the distal end portion of the attachment portion and an edge portion of the treatment instrument insertion hole portion in the central axis direction of the treatment instrument insertion hole portion and which prevents interference between the distal end portion of the attachment portion and the edge portion of the treatment instrument insertion hole portion.

11. The advance and retreat assist tool for the endoscopic treatment instrument according to claim 10, wherein
the distal end portion of the attachment portion has a cutout portion which is formed by the depression of a part of an edge portion of the distal end portion of the attachment portion in the central axis direction of the attachment portion, and
the distal end portion of the attachment portion is pressed into the treatment instrument insertion portion from the side surface of the treatment instrument insertion portion via the cutout portion in the diametrical direction of the body portion, and is thereby attached to the treatment instrument insertion portion.

12. The advance and retreat assist tool for the endoscopic treatment instrument according to claim 10, further comprising:
a distal end support portion which supports the distal end portion of the attachment portion;
an insertion support portion which supports the treatment instrument insertion portion; and
an urging portion which is connected to the distal end support portion and the insertion support portion and which urges at least one of the distal end portion of the attachment portion via the distal end support portion and the treatment instrument insertion portion via the insertion support portion toward the other.

13. The advance and retreat assist tool for the endoscopic treatment instrument according to claim 9, wherein
the distal end portion of the attachment portion has claw portions which extend along the central axis direction of the attachment portion and then bend toward the central axis of the attachment portion, and
the distal end portion of the attachment portion is attached to the treatment instrument insertion portion when the claw portions are caught on the edge portion of the treatment instrument insertion hole portion.

14. The advance and retreat assist tool for the endoscopic treatment instrument according to claim 1, wherein
the advance and retreat mechanism intervenes between the rotary portion and the first tubular member, and the advance and retreat mechanism converts a rotation force of the rotary portion to an advance and retreat force of the first tubular member, transmits the advance and retreat force to the first tubular member, and thereby advances and retreats the first tubular member when the rotary portion rotates.

15. The advance and retreat assist tool for the endoscopic treatment instrument according to claim 14, wherein the advance and retreat mechanism comprises
a protrusion portion which is provided straight along a diametrical direction of the first tubular member and which is engaged with circumferential surface of the first tubular member,
a second tubular member having a portion which is fitted into and thus fixed to the second hole portion to be provided along the third central axis of the first tubular member, and a long opening portion provided in a circumferential surface of the second tubular member, the first tubular member being inserted into the second tubular member so that the protrusion portion is inserted through the long opening portion, and
a third tubular member having a central axis provided along a central axis of the second tubular member, and a spiral opening portion provided in a circumferential surface of the third tubular member, the second tubular member being inserted into the third tubular member so that part of the spiral opening portion is in communication with part of the long opening portion and so that the protrusion portion which is inserted through the long opening portion is inserted into the spiral opening portion, the third tubular member being inserted into the rotary portion to rotate together with the rotary portion.

16. The advance and retreat assist tool for the endoscopic treatment instrument according to claim 15, wherein
the third tubular member rotates in response to a rotation of the rotary portion, and the spiral opening portion thereby rotates,
the protrusion portion moves in the long opening portion along a central axis direction of the second tubular member as a result of a rotation of the spiral opening portion,
the protrusion portion abuts on an edge portion of the long opening portion, so that the first tubular member with which the protrusion portion is engaged is prevented from rotating around the third central axis of the first tubular member, and
the spiral opening portion rotates, and the protrusion portion moves in the long opening portion, so that the first tubular member advances and retreats while a rotation of the first tubular member around the third central axis of the first tubular member is prevented.

17. The advance and retreat assist tool for the endoscopic treatment instrument according to claim 1, further comprising
a regulating mechanism which regulates the first tubular member when the first tubular member advances and retreats.

18. The advance and retreat assist tool for the endoscopic treatment instrument according to claim 1, wherein
a proximal end portion of the first tubular member projects outside a proximal end portion of the rotary portion along the direction of the third central axis of the first tubular member.

19. The advance and retreat assist tool for the endoscopic treatment instrument according to claim 1, further comprising
a support unit which supports the first tubular member so that the first tubular member is prevented from moving in a direction that intersects at right angles with the direction of the third central axis of the first tubular member.

* * * * *